(12) United States Patent
Ikebukuro et al.

(10) Patent No.: US 8,497,083 B2
(45) Date of Patent: Jul. 30, 2013

(54) FRUCTOSYL AMINO ACID OXIDASE

(75) Inventors: Kazunori Ikebukuro, Fuchu (JP); Sode Koji, Fuchu (JP)

(73) Assignees: Roche Diagnostics Operations, Inc., Indianapolis, IN (US), part interest; Ultizyme International, Ltd., part interest ( * ) Notice: Subject to any disclaimer, the term of this patent is extended or adjusted under 35 U.S.C. 154(b) by 0 days.

(21) Appl. No.: 13/365,487

(22) Filed: Feb. 3, 2012

(65) Prior Publication Data

US 2012/0208226 A1 Aug. 16, 2012

Related U.S. Application Data

(63) Continuation of application No. PCT/EP2010/004708, filed on Aug. 2, 2010.

(30) Foreign Application Priority Data

Aug. 3, 2009 (EP) ..................... 09009969

(51) Int. Cl.
| | |
|---|---|
| *C12Q 1/26* | (2006.01) |
| *C12Q 1/00* | (2006.01) |
| *C12N 11/00* | (2006.01) |
| *C12N 9/02* | (2006.01) |

(52) U.S. Cl.
USPC ........ 435/25; 435/174; 435/189; 204/403.14; 205/777.5

(58) Field of Classification Search
None
See application file for complete search history.

(56) References Cited

U.S. PATENT DOCUMENTS

| | | |
|---|---|---|
| 5,334,508 A | 8/1994 | Hoenes |
| 5,997,817 A | 12/1999 | Crismore et al. |
| 6,036,919 A | 3/2000 | Thym et al. |
| 7,008,799 B1 | 3/2006 | Zimmer et al. |

FOREIGN PATENT DOCUMENTS

| | | |
|---|---|---|
| EP | 1 291 416 A1 | 3/2004 |
| EP | 2 020 439 A1 | 2/2009 |
| EP | 1 626 088 A1 | 12/2010 |
| WO | WO 2004/113900 | 12/2004 |
| WO | WO 2007/055282 A2 | 5/2007 |

OTHER PUBLICATIONS

Fedrova et al. UniProt Jun. 16, 2009, Accession No. B6QMU0.*
Miura et al.; Protein Engineering, Design & Selection vol. 21, No. 4, pp. 233-239, 2008.
Miura et al.; Biotechnol. Letters (2006), vol. 28, No. 23, pp. 1895-1900 "Active site analysis of fructosyl amine oxidase . . . ".
Ferri et al.; "Cloning and expression of fructosyl-amine oxidase . . . " Marine Biotechnol. (N. Y, Nov. 2004, vol. 6, No. 6, pp. 625-632, XP002604707.
Kim Seungsu et al.; Biotechn. Letters, vol. 32, No. 8, Mar. 2010, pp. 1123-1129, XP 002604708 "Engineering of dye-mediated . . . ".
Hane et al.; The Plant Cell, vol. 19, pp. 3347-3368 (Nov. 2007) "Dothideomycete-Plant Interactions Illuminated by Genome Sequencing and EST Analysis of the . . . ".
Hirokawa et al.; Biochemical and Biophysical Research Communications 331, pp. 104-111 (2003) "Molecular cloning and expression of novel . . . ".
International Search Report; PCT/EP2010/004708, (May 26, 2011).

* cited by examiner

*Primary Examiner* — Nashaat Nashed
(74) *Attorney, Agent, or Firm* — Kevin J. Huser; Krieg DeVault LLP

(57) ABSTRACT

In one form, a mutant fructosyl amino acid oxidase modified at an amino acid residue involved in a proton relay system is provided. The mutant fructosyl amino acid oxidase has reduced oxidase activity while substantially maintaining its dehydrogenase activity. Other forms include an assay device and assay method for measuring glycated protein. Still, other forms include unique methods, techniques, systems and devices involving a mutant fructosyl amino acid oxidase.

19 Claims, 9 Drawing Sheets

| Activity (U/mg) | 4AA/TODB/POD [A] | | PMS/DCIP [B] | | B/A | |
|---|---|---|---|---|---|---|
| | 1mM f-αVal[A1] | 1mM f-αValHis[A2] | 1mM f-αVal[B1] | 1mM f-αValHis[B2] | B$_1$/A$_1$ | B$_2$/A$_2$ |
| Wild type | 1.3 (100%) | 0.15 (100%) | 1.2 (100%) | 0.099 (100%) | 0.92 | 0.66 |
| N56A | 0.24 (18%) | 0.086 (57%) | 2.2 (183%) | 0.26 (263%) | 9.2 | 3.0 |
| N56C | 0.22 (17%) | - | 1.5 (125%) | - | 6.8 | - |
| N56D | n.d | n.d | n.d | n.d | n.d | n.d |
| N56E | n.d | - | n.d | - | n.d | - |
| N56F | 0.11 (8.5%) | - | 0.92 (77%) | - | 8.4 | - |
| N56G | 0.054 (4.2%) | - | 0.23 (19%) | - | 4.3 | - |
| N56H | 0.061 (4.7%) | 0.020 (13%) | 0.33 (28 %) | 0.043 (43%) | 5.4 | 2.2 |
| N56I | n.d | - | 0.049 (4.1%) | - | - | - |
| N56K | 0.060 (4.6%) | - | 0.35 (29%) | - | 5.8 | - |
| N56L | 0.0051(0.39%) | - | 0.041 (3.4%) | - | 8.0 | - |
| N56M | 0.17 (13%) | - | 1.6 (133%) | - | 9.4 | - |
| N56P | n.d | - | n.d | - | n.d | - |
| N56Q | 0.055 (4.2%) | - | 0.27 (23%) | - | 5.0 | - |
| N56R | 0.032 (2.5%) | - | 0.16 (13%) | - | 5.0 | - |
| N56S | 0.53 (41%) | - | 1.4 (117%) | - | 5.4 | - |
| N56T | 0.077 (5.9%) | - | 0.32 (27%) | - | 2.6 | - |
| N56V | 0.049 (3.8%) | - | 0.72 (60%) | - | 14.7 | - |
| N56W | 0.015 (1.2%) | - | 0.056 (4.7%) | - | 3.7 | - |
| N56Y | 0.032 (2.5%) | - | 0.16 (13%) | - | 5.0 | - | n.d ; not detected, - ; did not measured

Fig. 4

| | | 4AA/TODB/POD (Oxidase) | | | PMS/DCIP (Dehydrogenase) | | | B/A |
|---|---|---|---|---|---|---|---|---|
| | | $K_m$ (mM) | $V_{max}$ (A) (U·mg⁻¹) | $V_{max}/K_m$ (U·mg⁻¹·mM⁻¹) | $K_m$ (mM) | $V_{max}$ (B) (U·mg⁻¹) | $V_{max}/K_m$ (U·mg⁻¹·mM⁻¹) | |
| PnFPOX (Crude) | WT | 0.61 | 2.6 (100 %) | 4.3 (100 %) | 0.91 | 2.2 (100 %) | 2.4 (100 %) | 0.85 |
| | N56A | 0.12 | 0.28 (11 %) | 2.3 (53 %) | 1.2 | 4.6 (209 %) | 3.8 (158 %) | 16 |
| | N56C | 0.14 | 0.29 (11 %) | 2.1 (49 %) | 0.99 | 3.1 (141 %) | 3.1 (129 %) | 11 |
| | N56F | 0.086 | 0.13 (5.0 %) | 1.5 (35 %) | 0.64 | 1.6 (73 %) | 2.5 (104 %) | 12 |
| | N56M | 0.08 | 0.19 (7.3 %) | 2.4 (56 %) | 0.75 | 3.4 (155 %) | 4.5 (188 %) | 18 |
| | N56S | 0.29 | 0.73 (28 %) | 2.5 (58 %) | 0.98 | 2.9 (132 %) | 3.0 (125 %) | 4 |
| | N56V | 0.12 | 0.059 (2.3 %) | 0.49 (11 %) | 1.1 | 1.5 (68 %) | 0.91 (38 %) | 25 |

Fig.5

|  |  | 4AA/TODB/POD (Oxidase) | | | PMS/DCIP (Dehydrogenase) | | | B/A |
| --- | --- | --- | --- | --- | --- | --- | --- | --- |
|  |  | $K_m$ (mM) | $V_{max}$ (A) (U·mg$^{-1}$) | $V_{max}/K_m$ (U·mg$^{-1}$·mM$^{-1}$) | $K_m$ (mM) | $V_{max}$ (B) (U·mg$^{-1}$) | $V_{max}/K_m$ (U·mg$^{-1}$·mM$^{-1}$) |  |
| Amadori-ase II (Purified) | WT | 3 | 18 (100 %) | 6.0 (100 %) | 4 | 20 (100%) | 5.0 (100 %) | 1.1 |
|  | N52A | 1.1 | 1.7 (9.4 %) | 1.5 (25 %) | 2.2 | 4.4 (22%) | 2.0 (40 %) | 2.6 |
| Amadori-ase II (Crude) | WT | 2.2 | 1.4 (100 %) | 0.64 (100 %) | 3.1 | 1.3 (100%) | 0.43 (100 %) | 0.93 |
|  | N52A | 1.7 | 0.32 (23 %) | 0.19 (30 %) | 2.8 | 0.75 (58%) | 0.27 (63 %) | 2.3 |

Fig. 8

FRUCTOSYL AMINO ACID OXIDASE

CROSS-REFERENCE TO RELATED APPLICATIONS

This application is a continuation of International Application No. PCT/EP/2010/004708 filed Aug. 2, 2010, which claims priority to European Patent Application No. 09009969.8 filed Aug. 3, 2009. Each of the referenced applications is incorporated herein by reference in its entirety.

FIELD OF THE INVENTION

The present application relates to a fructosyl amino acid oxidase (also called fructosylamine oxidase) for use in a kit and a sensor for the measurement of glycated proteins, such as glycated albumin, fructosyl peptides, HbA1c and fructosyl valine (FV). More particularly, but not exclusively, the present application relates to a mutant fructosyl amino acid oxidase having reduced oxidase activity.

BACKGROUND

A glycated protein is generated non-enzymatically via a covalent bond between an amino group on a protein and the reducing terminal of a sugar, and is also referred to as an Amadori compound. In blood, glucose is bound to valine at the N-terminal of the β-chain of hemoglobin to generate glycated hemoglobin (glycohemoglobin; HbA1c). The abundance ratio of HbA1c to hemoglobin is higher in patients suffering from diabetes mellitus as compared with a normal healthy individual, and the concentration of HbA1c in blood is known to reflect the blood-sugar level during the past several weeks. Thus, concentration of HbA1c in blood is quite important in clinical tests for diagnosis of diabetes mellitus and in blood-sugar control of patients suffering from diabetes mellitus. The HbA1c concentration in blood may be measured using an enzyme having specificity to fructosyl valine or fructosyl valyl histidine.

Fructosyl amino acid oxidases have been isolated from various kinds of strains and it has been suggested that glycated proteins such as glycated albumin, HbA1c and fructosyl amino acids may be analyzed using such enzymes (JP A 61-268, 178; JP A 61-280, 297; JP A 03-155, 780; JP A 05-192, 193; JP A 07-289, 253; JP A 08-154, 672; JP A 2001-95598; JP A 2003-79386; JP A 2003-235585; Agric. Biol. Chem., 53(1), 103-110, 1989; Agric. Biol. Chem., 55(2), 333-338, 1991; J. Biol. Chem., 269(44), 27297-27301, 1994; Appl. Environ. Microbiol., 61(12), 4487-4489, 1995; Biosci. Biotech. Biochem., 59(3), 487-491, 1995; J. Biol. Chem., 270(1), 218-224, 1995; J. Biol. Chem., 271(51), 32803-32809, 1996; and J. Biol. Chem., 272(6), 3437-3443, 1997).

Fructosyl amino acid oxidase is a FAD-dependent enzyme which catalyzes a reaction where fructosyl amino acid is oxidized to generate 2-keto-D-glucose and the corresponding amino acid, while generating the reduced form of FAD (FADH2). FADH2 in turn transmits electrons to an electron acceptor and is converted to its oxidized form. In the presence of oxygen, FADH2 preferentially transmits electrons to the oxygen molecule rather than to artificial electron acceptors (also referred to as mediators or electron mediators). Thus, when a fructosyl amino acid is assayed by fructosyl amino acid oxidase with mediators, the assay results will be greatly affected by the dissolved oxygen level in the reaction system. This impact may be undesirable in clinical tests of blood samples by a point-of-care testing device utilizing an artificial electron acceptor. In some forms, it is desirable for the enzyme used for enzyme sensor strips employing artificial electron mediators to have low activity toward oxygen.

Accordingly, one non-limiting object of the present application is to provide an enzyme, such as a fructosyl amino acid oxidase, whose activity is less affected by the dissolved oxygen level. Further objects, embodiments, forms, features, advantages, aspects, and benefits shall become apparent from the following description and drawings.

SUMMARY

In one embodiment, an enzyme, such as a fructosyl amino acid oxidase, whose activity is less affected by the dissolved oxygen level is provided. More specifically, this has been achieved by reducing the oxidase activity of an enzyme that in its wild-type form predominantly shows an oxidase activity and, in some forms, also increasing the enzyme's dehydrogenase activity. As will be described in more detail below, this has been achieved by mutating the wild type enzyme.

Various mutants of a fructosyl amino acid oxidase have been prepared, and it has been surprisingly found that a certain type of mutants exhibit reduced oxidase activity while substantially retaining dehydrogenase activity, in particular dye-mediated dehydrogenase activity.

In one embodiment, a mutant fructosyl amino acid oxidase is provided which has been modified at a position corresponding to the position 56 of the amino acid sequence set forth in SEQ ID NO: 1 by substituting the amino acid residue Asn with an amino acid residue selected from Ala, Cys, Phe, Met, Ser and Val.

In another embodiment, a mutant fructosyl amino acid oxidase has a reduced oxidase activity as compared to the wild-type fructosyl amino acid oxidase. In one aspect, the mutant fructosyl amino acid oxidase may have an increased dehydrogenase activity compared to the wild-type fructosyl amino acid oxidase. In another embodiment, a mutant fructosyl amino acid oxidase has an oxidase activity of 30% or less of that of the wild-type fructosyl amino acid oxidase. In one aspect of this embodiment, the mutant fructosyl amino acid oxidase may have a dehydrogenase activity of 50% or more of the wild-type fructosyl amino acid oxidase. In another embodiment, a mutant fructosyl amino acid oxidase has an increased dehydrogenase activity compared to the wild-type fructosyl amino acid oxidase.

In another embodiment, a mutant fructosyl amino acid oxidase has an amino acid sequence selected from the group consisting of SEQ ID NOs: 1-16 wherein the amino acid residue Asn at a position corresponding to the position 56 of the amino acid sequence set forth in SEQ ID NO: 1 is substituted with an amino acid residue selected from Ala, Cys, Phe, Met, Ser and Val. In one particular embodiment, a mutant fructosyl amino acid oxidase has the amino acid sequence set forth in SEQ ID NO: 1 wherein the amino acid residue Asn at the position 56 is substituted with an amino acid residue selected from Ala, Cys, Phe, Met, Ser and Val. In one aspect, the amino acid residues Ser Gly Tyr Gln Ala Leu Val Asp Ala Gly Leu Asp Ala Thr Asn Glu at the positions 109-124 of SEQ ID NO: 1 are replaced with the sequence: Lys Gln Tyr Gln Ala Leu His Asp Ala Gly Ala Gly Leu Glu Lys Thr His Ala of SEQ ID NO: 16. In another particular embodiment, a mutant fructosyl amino acid oxidase has the amino acid sequence set forth in SEQ ID NO: 2 wherein the amino acid residue Asn at the position 47 is substituted with an amino acid residue selected from Ala, Cys, Phe, Met, Ser and Val. In still another particular embodiment, a mutant fructosyl amino acid oxidase has the amino acid sequence set forth in SEQ ID NO: 3 wherein the amino acid residue Asn at the position 52 is substituted with an amino acid residue selected from Ala, Cys, Phe, Met, Ser and Val. In yet another particular embodiment, a mutant fructosyl amino acid oxidase has the amino acid sequence set forth in SEQ ID NO: 7 wherein the amino acid residue Asn at the position 56 is substituted with an amino acid residue selected from Ala, Cys, Phe, Met, Ser and Val. In one aspect, the amino acid residues Ile Arg Leu Arg Asn Lys Val Asp Leu Gln Met Ser at the positions 61-72 of SEQ ID NO: 7 are replaced with the sequence Val Ser Leu Arg Asn Pro Val Asp Leu Gln Leu Ala of SEQ ID NO: 13.

In another aspect, an isolated polynucleotide encoding a mutant fructosyl amino acid oxidase disclosed herein is provided.

In yet another aspect, a vector including the polynucleotide described above is provided.

In still another aspect, a host cell transformed with a vector described above is provided.

In another aspect, a method for assaying a glycated protein in a sample includes contacting the sample with a fructosyl amino acid oxidase disclosed herein and measuring the amount of the glycated protein oxidized by fructosyl amino acid oxidase.

In still another aspect, a method for assaying HbA1c includes digesting HbA1c in a sample to generate fructosyl valine or fructosyl valyl histidine, contacting the fructosyl valine or fructosyl valyl histidine with a fructosyl amino acid oxidase disclosed herein, and measuring the amount of oxidized fructosyl valine or fructosyl valyl histidine.

In another aspect, a device for assaying fructosyl valine, fructosyl valyl histidine, HbA1c or fructosyl hexapeptide in a sample includes a fructosyl amino acid oxidase disclosed herein and an electron transfer mediator.

In yet another aspect, a kit for assaying fructosyl valine, fructosyl valyl histidine, HbA1c or fructosyl hexapeptide in a sample includes a fructosyl amino acid oxidase disclosed herein and an electron transfer mediator.

In another aspect, an enzyme electrode includes a fructosyl amino acid oxidase disclosed herein which is immobilized on the electrode.

In another aspect, an enzyme sensor for assaying fructosyl valine, fructosyl valyl histidine, HbA1c or fructosyl hexapeptide includes the enzyme electrode described above as a working electrode.

In yet another aspect, a mutant fructosyl amino acid oxidase has the amino acid sequence set forth in SEQ ID NO: 1 wherein the amino acid residues Val Ser Leu Arg Asn Pro Val Asp Leu Gln Leu Ala at positions 61-72 of SEQ ID NO: 1 are replaced with the sequence: Ile Arg Leu Arg Asn Lys Val Asp Leu Gln Met Ser of SEQ ID NO: 14. In yet another aspect, a mutant fructosyl amino acid oxidase has the amino acid sequence set forth in SEQ ID NO: 1 wherein the amino acid residues Ser Gly Tyr Gln Ala Leu Val Asp Ala Gly Leu Asp Ala Thr Asn Glu at positions 109-124 of SEQ ID NO: 1 are replaced with the sequence: Lys Gln Tyr Gln Ala Leu His Asp Ala Gly Ala Gly Leu Glu Lys Thr His Ala of SEQ ID NO: 16. In yet another aspect, a mutant fructosyl amino acid oxidase has the amino acid sequence set forth in SEQ ID NO: 7 wherein the amino acid residues Ile Arg Leu Arg Asn Lys Val Asp Leu Gln Met Ser at positions 61-72 of SEQ ID NO: 7 are replaced with the sequence: Val Ser Leu Arg Asn Pro Val Asp Leu Gln Leu Ala of SEQ ID NO: 13. In yet another aspect, a mutant fructosyl amino acid oxidase has the amino acid sequence set forth in SEQ ID NO: 7 wherein the amino acid residues Lys Gln Tyr Gln Ala Leu His Asp Ala Gly Ala Gly Leu Glu Lys Thr His Ala at positions 109-126 of SEQ ID NO: 1 are replaced with the sequence: Ser Gly Tyr Gln Ala Leu Val Asp Ala Gly Leu Asp Ala Thr Asn Glu of SEQ ID NO: 15.

Other aspects include unique methods, techniques, systems and devices involving a mutant fructosyl amino acid oxidase.

Further embodiments, forms, objects, features, advantages, aspects, and benefits shall become apparent from the following description and drawings.

BRIEF DESCRIPTION OF THE DRAWINGS

FIG. 4 shows the oxidase and dehydrogenase activity of crude PnFPOX (SEQ ID NO: 1) wild-type and Asn56 mutants.

FIG. 5 shows kinetic parameters of PnFPOX Asn56 mutants.

FIG. 8 shows the kinetic parameters of purified Amadoriase II (SEQ ID NO: 3) wild type and N52A mutant.

DETAILED DESCRIPTION

Figure 1:
FIG. 1 shows alignment of the amino acid sequence around N-terminus of some of the eukaryotic FAODs.

Fructosyl amino acid oxidases (FAOD) are known to exist in various eukaryotic and prokaryotic strains. Table 1 shows some non-limiting examples of the FAODs isolated or predicted to date.

TABLE 1

| FAOD | Origin | Reference | SEQ ID NO |
| --- | --- | --- | --- |
| PnFPOX | *Phaeosphaeria nodorum* | GenBank: XP_001798711.1 | 1 |
| N1-1 FAOD | *Pichia* sp. N1-1 | GenBank: AAP83789.1 | 2 |
| Amadoriases II | *Aspergillus fumigatus* | GenBank: AAC49711.1 | 3 |
| FAOD-P | *Penicillum janthinelum* AKU 3413 | GenBank: CAA70219.1 | 4 |
| FAOD-U | *Ulocladium* sp. JS-103 | GenBank: BAE93140.1 | 5 |
| FPOX-E | *Eupenicillum terrenum* ATCC 18547 | GenBank: BAD00185.1 | 6 |
| FPOX-C | *Coniochaeta* sp. NISL 9330 | GenBank: BAD00186.1 | 7 |
| FAOD-F | *Fusarium oxysporum* NBRC 9972 | JP A 10-201473 | 8 |
| FAOD-A | *Aspergillus terreus* GP1 | GenBank: CAA70218.1 | 9 |
| FAOD-Ao1 | *Aspergillus oryzae* | GenBank: BAD54824.1 | 10 |
| Amadoriases I | *Aspergillus fumigatus* | GenBank: AAB88209.1 | 11 |
| FAOD-Ao2 | *Aspergillus oryzae* | GenBank: BAD54825.1 | 12 |

The eukaryotic FAODs may be grouped according to substrate specificity: (i) preference for α-fructosyl amino acids (FAOD-P (SEQ ID NO: 4), FAOD-U (SEQ ID NO: 5), FPOX-E (SEQ ID NO: 6), FPOX-C (SEQ ID NO; 7), and PnFPOX (SEQ ID NO: 1)), (ii) preference for ε-fructosyl amino acids (FAOD-F (SEQ ID NO: 8), FAOD-A (SEQ ID NO: 9), Amadoriase I (SEQ ID NO: 11), and FAOD-Ao1 (SEQ ID NO: 10)), and (iii) similar activity with both α- and ε-glycated amino acids (Amadoriase II (SEQ ID NO: 3), FAOD-Ao2 (SEQ ID NO: 12), and N1-1 FAOD (SEQ ID NO: 2)). In general, FAODs active on α-fructosyl amino acids will be useful in assaying α-fructosyl valine and HbA1c, and those active on ε-fructosyl amino acid will be useful in assaying α-fructosyl lysine and glycated albumin. Those skilled in the art will appreciate that introducing a mutation into the enzyme may alter its preference for α- or ε-fructosyl amino acid.

The present applications provides, amongst other things, a mutant fructosyl amino acid oxidase modified at a position corresponding to the position 56 of the amino acid sequence set forth in SEQ ID NO: 1 (PnFPOX) by substituting the amino acid residue Asn with an amino acid residue selected from Ala, Cys, Phe, Met, Ser and Val.

The term "mutant" of a protein as used herein refers to a variant protein containing substitution in one or more of the amino acid residues on the protein at the indicated position(s). The term mutant is also used for a polynucleotide encoding such as a mutant protein.

The phrase "a position corresponding to" as used herein means the position of an amino acid residue in a query amino acid sequence that is aligned with the amino acid residue in a reference amino acid sequence using a software AlignX® of Vector NTI with default parameters (available from Invitrogen; see, Lu, G., and Moriyama, E. N. (2004) Vector NTI, a balanced all-in-one sequence analysis suite. Brief Bioinform 5, 378-88). Thus, "Asn residue at a position corresponding to the position 56 of the amino acid sequence set forth in SEQ ID NO: 1" means the Asn residue in a query amino acid sequence that is aligned with Asn56 of SEQ ID NO: 1 when the query amino acid sequence is aligned with SEQ ID NO:1 using AlignX® of Vector NTI with default parameters. It should be noted that the Asn47 of SEQ ID NO: 1 itself is also encompassed by this term.

FIG. 1 shows alignment of the amino acid sequence within the conserved region near the N-terminus of some of the eukaryotic FAODs (FAOD-P (SEQ ID NO: 4) from Penicillum janthinelum AKU 3413, FAOD-U (SEQ ID NO: 5) from *Ulocladium* sp. JS-103, FPOX-E (SEQ ID NO: 6) from Eupenicillum terrenum ATCC 18547, FPOX-C (SEQ ID NO: 7) from *Coniochaeta* sp. NISL 9330, PnFPOX (SEQ ID NO: 1) from *Phaeosphaeria nodorum*, FAOD-F (SEQ ID NO: 8) from *Fusarium oxysporum* NBRC 9972, FAOD-A (SEQ ID NO: 9) from *Aspergillus terreus* GP1, Amadoriases I (SEQ ID NO: 11) from *Aspergillus fumigatus*, FAOD-Ao1 (SEQ ID NO: 10) from *Aspergillus oryzae*, Amadoriases II (SEQ ID NO: 3) from *Aspergillus fumigatus*, FAOD-Ao2 (SEQ ID NO: 12) from *Aspergillus oryzae* and N1-1 FAOD (SEQ ID NO: 2) from *Pichia* sp. N1-1). The entire sequence of these FAODs are set forth in SEQ ID NOs: 1-12. Alignment was created using AlignX® application of Vector NTI suite 6.0. The arrowhead indicates the residues corresponding to the Asn47 of N1-1 FAOD (SEQ ID NO: 2). The number in the parentheses indicates the position of the leftmost "P" of FIG. 1 in each amino acid sequence represented by the SEQ ID NOs. Those skilled in the art will appreciate that other alignment software programs such as Blast will provide the same or substantially the same alignment.

It is evident from FIG. 1 that the amino acid sequences in the region containing Asn47 of N1-1 FAOD (SEQ ID NO: 2) are highly conserved among eukaryotic FAODs.

Accordingly, a person skilled in the art can easily identify the Asn residue corresponding to the Asn47 of N1-1 FAOD (SEQ ID NO: 2) within the conserved region using commercially available software programs for sequence alignment, and understand that a mutant fructosyl amino acid oxidase may be prepared by introducing modification on that Asn residue.

In another embodiment, a mutant fructosyl amino acid oxidase has an amino acid sequence selected from the group consisting of SEQ ID NOs: 1-15 wherein the amino acid residue Asn at a position corresponding to the position 56 of the amino acid sequence set forth in SEQ ID NO: 1 is substituted with an amino acid residue selected from Ala, Cys, Phe, Met, Ser and Val. In one particular form, the Asn residue is substituted with Ala.

In one embodiment, a mutant fructosyl amino acid oxidase has the amino acid sequence set forth in SEQ ID NO: 1 (PnFPOX) wherein the amino acid residue Asn at the position 56 is substituted with an amino acid residue selected from Ala, Cys, Phe, Met, Ser and Val. In one particular form, the Asn residue is substituted with Ala. In another embodiment, a mutant fructosyl amino acid oxidase has the amino acid sequence set forth in SEQ ID NO: 2 (N1-1) wherein the amino acid residue Asn at the position 47 is substituted with an amino acid residue selected from Ala, Cys, Phe, Met, Ser and Val. In yet another embodiment, a mutant fructosyl amino acid oxidase has the amino acid sequence set forth in SEQ ID NO: 3 (AmadoriaseII) wherein the amino acid residue Asn at the position 52 is substituted with an amino acid residue selected from Ala, Cys, Phe, Met, Ser and Val.

Figure 2:
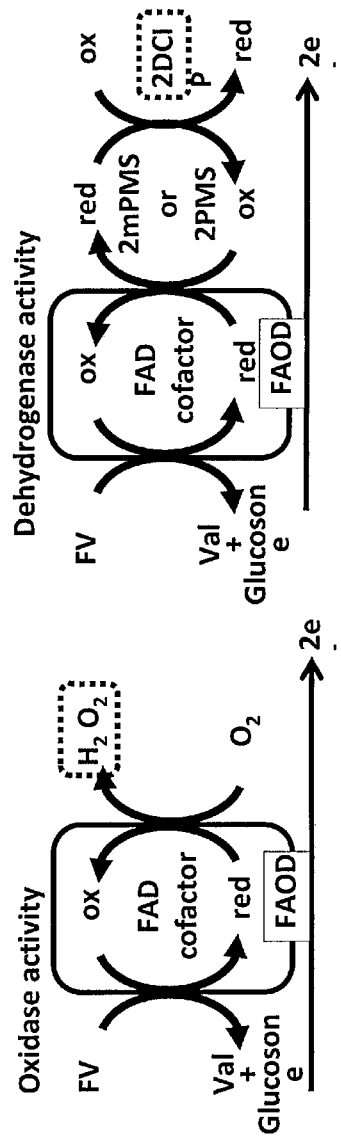
FIG. 2 shows the reaction system of fructosyl amino acid oxidase.

In one form, a mutant fructosyl amino acid oxidase exhibits decreased oxidase activity while substantially retaining dehydrogenase activity. FIG. 2 illustrates the reaction scheme of fructosyl amino acid oxidase.

As used herein "oxidase activity" is an enzymatic activity (Vmax) of the fructosyl amino acid oxidase to catalyze oxidation of fructosyl amino acid to generate 2-keto-D-glucose and the corresponding amino acid while utilizing oxygen as an electron acceptor. The oxidase activity may be assayed by measuring the amount of generated $H_2O_2$ by any methods known in the art, including by way of non-limiting example, reagents for $H_2O_2$ detection such as 4AA/i/POD (4-aminoantipyrine/N,N-Bis(4-sulfobutyl)-3-methylaniline disodium salt/horseradish peroxidase) or by Pt electrode. As used herein in the context of the relative or quantitative activity, the oxidase activity is specifically defined to be the mole amount of the substrate (fructosyl amino acid) oxidized per unit time measured by the amount of generated $H_2O_2$ at 25° C. in 10 mM PPB, pH 7.0, 1.5 mM TODB, 2 U/ml horseradish peroxidase (POD), and 1.5 mM 4-aminoantipyrine (4AA). The formation of quinoneimine dye may be measured spectrophotometrically at 546 nm.

As used herein, "dehydrogenase activity" is an enzymatic activity (Vmax) of the fructosyl amino acid oxidase to catalyze oxidation of fructosyl amino acid to generate 2-keto-D-glucose and the corresponding amino acid while utilizing an electron mediator other than oxygen as an electron acceptor. The dehydrogenase activity may be assayed by measuring the amount of electrons transferred to the mediator using, for example, one of mPMS/DCIP (1-methoxy-5-methylphenazinium methylsulfate/2,6-dichloroindophenol), cPES (trifluoro-acetate-1-(3-carboxy-propoxy)-5-ethyl-phenanzinium, NA BM31_1144 (N,N-bis-(hydroxyethyl)-3-methoxynitrosoaniline hydrochloride, NA BM31_1008 (N,N-bis-hydroxyethyl-4-nitrosoaniline) and N—N-4-dimethyl-nitrosoaniline.

As used herein in the context of the relative or quantitative activity, the dehydrogenase activity is specifically defined to be the mole amount of the substrate (fructosyl amino acid)

oxidized per unit time measured by the amount of electrons transferred to the mediator at 25° C. in 10 mM PPB (pH 7.0), 0.6 mM DCIP, and 6 mM methoxy PMS (mPMS).

In one form, a mutant fructosyl amino acid oxidase has a reduced oxidase activity as compared to the wild-type fructosyl amino acid oxidase, while substantially retaining the dehydrogenase activity.

In one particular form, a mutant fructosyl amino acid oxidase has an oxidase activity of 50% or less of that of the wild-type fructosyl amino acid oxidase. In another form, a mutant fructosyl amino acid oxidase has an oxidase activity of 40% or less of that of the wild-type fructosyl amino acid oxidase. In still another form, a mutant fructosyl amino acid oxidase has an oxidase activity of 30% or less of that of the wild-type fructosyl amino acid oxidase. In another form, a mutant fructosyl amino acid oxidase has an oxidase activity of 20% or less of that of the wild-type fructosyl amino acid oxidase. In yet another form, a mutant fructosyl amino acid oxidase has an oxidase activity of 15% or less of that of the wild-type fructosyl amino acid oxidase. In another form, a mutant fructosyl amino acid oxidase has a dehydrogenase activity of 50% or more of the wild-type fructosyl amino acid oxidase. In still another form, a mutant fructosyl amino acid oxidase has a dehydrogenase activity of 70% or more of the wild-type fructosyl amino acid oxidase. In another form, a mutant fructosyl amino acid oxidase has a dehydrogenase activity of 90% or more of the wild-type fructosyl amino acid oxidase. In yet another form, a mutant fructosyl amino acid oxidase has a dehydrogenase activity of 100% or more of the wild-type fructosyl amino acid oxidase. In still another form, a mutant fructosyl amino acid oxidase has a dehydrogenase activity of more than 100% of the wild-type fructosyl amino acid oxidase.

In the wild-type fructosyl amino acid oxidase, the oxidase activity and dehydrogenase activity is in a comparable level, with the ratio of dehydrogenase/oxidase activity being between about 0.8 to 1.2. When dissolved oxygen is present in the assay system, the electrons generated by the oxidation of the substrate will be preferentially transferred to the oxygen. Thus the enzyme activity measured in the presence of electron mediator will be greatly affected by the dissolved oxygen concentration. In contrast, in one form a mutant fructosyl amino acid oxidase has a ratio of dehydrogenase/oxidase activity of about 2.0 or more. In another form, a mutant fructosyl amino acid oxidase has a ratio of dehydrogenase/oxidase activity of about 4.0 or more. In yet another form, a mutant fructosyl amino acid oxidase has a ratio of dehydrogenase/oxidase activity of about 10 or more. In another form, a mutant fructosyl amino acid oxidase has a ratio of dehydrogenase/oxidase activity of about 20 or more. In still another form, a mutant fructosyl amino acid oxidase has a ratio of dehydrogenase/oxidase activity of about 40 or more. Since the dehydrogenase activity exceeds the oxidase activity, the enzyme activity of the fructosyl amino acid oxidase will be less affected by the dissolved oxygen concentration, which may be, for example, desirable for applications in which the fructosyl amino acid oxidase is utilized in clinical diagnosis of a blood sample.

In another aspect, a fructosyl amino acid oxidase where one or more loop regions are modified or mutated is provided. PnFPOX (SEQ ID NO: 1) shows oxidase activity toward fructosyl hexapeptide at a level of less 1% of the activity compared with FVH, whereas FPOX-C (SEQ ID NO: 7) shows no activity. On the other hand, FPOX-C (SEQ ID NO: 7) shows higher activity toward FVH than PnFPOX (SEQ ID NO: 1). From comparison of the amino acid sequence of both oxidases, significant difference between FAOD and FPOX is found in their loop regions.

Loop 1 Region
PnFPOX (SEQ ID NO: 1): (61) Val Ser Leu Arg Asn Pro Val Asp Leu Gln Leu Ala (72) (SEQ ID NO: 13)
FPOX-C (SEQ ID NO: 7): (61) Ile Arg Leu Arg Asn Lys Val Asp Leu Gln Met Ser (72) (SEQ ID NO: 14)
Loop 2 Region
PnFPOX (SEQ ID NO: 1): (109) Ser Gly Tyr Gln Ala Leu Val Asp Ala Gly Leu Asp Ala Thr Asn Glu (124) (SEQ ID NO: 15)
FPOX-C (SEQ ID NO: 7): (109) Lys Gln Tyr Gln Ala Leu His Asp Ala Gly Ala Gly Leu Glu Lys Thr His Ala (126) (SEQ ID NO: 16)

At the loop 1 region (12aa) 5 amino acid residues are different between PnFPOX (SEQ ID NO: 1) and FPOX-C (SEQ ID NO: 7). At the loop 2 region (16aa), 2 amino acid insertions and 7 amino acid substitutions are observed.

It has been surprisingly found that some chimeric loop mutants where loop regions of 1 PnFPOX (SEQ ID NO: 1) and FPOX-C (SEQ ID NO: 7) are exchanged for each other showed improved activity. As shown in Example 8 below, PnFPOX (SEQ ID NO: 1) where its loop 2 region (SEQ ID NO: 15) is replaced by FPOX-C (SEQ ID NO: 7) loop 2 region (SEQ ID NO: 16) shows higher oxidase activity toward FV, FVH and fructosyl hexapeptide (F—HP) than the wild type PnFPOX (SEQ ID NO: 1). FPOX-C (SEQ ID NO: 7) where its loop 1 region (SEQ ID NO: 14) is replaced by PnFPOX (SEQ ID NO: 1) loop 1 region (SEQ ID NO: 13) shows oxidase activity toward F—HP, which is not detected in the wild type FPOX-C (SEQ ID NO: 7). In addition, chimeric loop mutants having N56A mutation also show decreased oxidase activity and increased dehydrogenase activity, as observed in the N56A mutants derived from PnFPOX (SEQ ID NO: 1) and FPOX-C (SEQ ID NO: 7). In one particular form, the chimeric loop mutant is PnFPOX (SEQ ID NO: 1) where the loop 2 region (SEQ ID NO: 15) is substituted with the loop 2 region (SEQ ID NO: 16) from FPOX-C (SEQ ID NO: 7), and Asn56 is substituted with Ala. In another particular form, the chimeric loop mutant is FPOX-C (SEQ ID NO: 7) where the loop 1 region (SEQ ID NO: 14) is substituted with the loop 1 region (SEQ ID NO: 13) from PnFPOX (SEQ ID NO: 1), and Asn56 is substituted with Ala. These results suggest that a combination of the loop 1 region (SEQ ID NO: 13) from PnFPOX (SEQ ID NO: 1) and the loop 2 region (SEQ ID NO: 16) from FPOX-C (SEQ ID NO: 7) provides higher activity toward fructosyl valine and fructosyl valyl histidine as well as toward fructosyl hexapeptide.

In another aspect, an isolated polynucleotide encoding a mutant fructosyl amino acid oxidase disclosed herein is provided. The nucleotide sequence of polynucleotides coding for fructosyl amino acid oxidase may be easily obtained from public databases. The polynucleotide encoding the wild type fructosyl amino acid oxidase may be cloned from the genome of respective organisms using PCR or other known techniques. Mutations may be introduced by site-directed mutagenesis, PCR mutagenesis or any other techniques well known in the art. The Asn residue to be mutated may be identified using any sequence alignment software available in the art. Alternatively, polynucleotide coding for the mutant fructosyl amino acid oxidase may be prepared by PCR using a series of chemically synthesized oligonucleotides, or fully synthesized.

A mutated fructosyl amino acid oxidase may be prepared by inserting the mutant gene into an appropriate expression vector and introducing the vector into an appropriate host cell, such as *E. coli* cells. The transformant is cultured and the fructosyl amino acid oxidase expressed in the transformant may be collected from the cells or culture medium.

The recombinant fructosyl amino acid oxidase thus obtained may be purified by any of the purification techniques known in the art, including but not limited to ion exchange column chromatography, affinity chromatography, liquid chromatography, filtration, ultrafiltration, salt precipitation, solvent precipitation, immunoprecipitation, gel electrophoresis, isoelectric electrophoresis and dialysis.

In yet another aspect, a vector includes the polynucleotide encoding the mutant fructosyl amino acid oxidase, a host cell transformed with such a vector, and a method for preparing the mutant fructosyl amino acid oxidase by culturing the transformant, and collecting and purifying the mutant fructosyl amino acid oxidase from the culture.

In another aspect, a method for assaying a glycated protein in a sample is provided. The method includes contacting the sample with a fructosyl amino acid oxidase disclosed herein and measuring the amount of the glycated protein oxidized by the fructosyl amino acid oxidase. Glycated proteins which may be assayed in this manner include, for example, fructosyl valine, fructosyl valyl histidine, HbA1c, fructosyl hexapeptide, glycated albumin and other fructosyl amino acids. In still another aspect, a method for assaying HbA1c includes digesting HbA1c in a sample to generate fructosyl valine, contacting the fructosyl valine with a fructosyl amino acid oxidase disclosed herein, and measuring the amount of oxidized fructosyl valine.

In another aspect, a device for assaying fructosyl valine, fructosyl valyl histidine, HbA1c, fructosyl hexapeptide or glycated albumin in a sample includes a fructosyl amino acid oxidase disclosed herein and an electron transfer mediator.

The assay device may have a structure similar to any conventional, commercially available amperometric biosensor test strips for monitoring blood glucose levels. One non-limiting example of such a device has two electrodes (a working electrode and a reference or counter electrode) positioned on an insulating substrate, a reagent port and a sample receiver. The reagent port contains a mutated fructosyl amino acid oxidase disclosed herein and a mediator. When a sample such as a blood sample is added to the sample receiver, fructosyl amino acid contained in the sample will react with fructosyl amino acid oxidase to generate current, which is indicative of the amount of fructosyl amino acid in the sample. Non-limiting examples of electrochemical sensors suited for the determination of enzyme substrates are known, for example, from International Patent Publication No. WO 2004/113900 and U.S. Pat. No. 5,997,817. As an alternative to electrochemical sensors, optical detection technologies might be used. Typically, such optical devices are based on color changes that occur in a reagent system comprising the enzyme, an electron transfer mediator and an indicator. The color changes can be quantified using fluorescence, absorption or remission measurements. Non-limiting examples of optical devices suited for the determination of enzyme substrates are known, for example, from U.S. Pat. Nos. 7,008,799, 6,036,919, and 5,334,508.

In yet another aspect, a kit for assaying fructosyl valine, fructosyl valyl histidine, HbA1c or fructosyl hexapeptide in a sample includes a fructosyl amino acid oxidase disclosed herein and an electron transfer mediator.

A kit for the measurement of fructosyl valine or fructosyl valyl histidine may be constructed using an enzyme disclosed herein. In addition to the fructosyl amino acid oxidase, the kit contains a buffer necessary for the measurement, an appropriate mediator and, if necessary, enzymes such as peroxidase, standard solution of fructosyl valine or fructosyl valyl histidine or a derivative thereof for the preparation of a calibration curve, and an instructions for use. The fructosyl amino acid oxidase may be provided in various forms, such as for example, a freeze-dried reagent or a solution in an appropriate storage solution.

It is also possible to construct a glycated albumin, HbA1c or fructosyl hexapeptide assay kit using an enzyme disclosed herein. Glycated albumin, HbA1c or fructosyl hexapeptide is enzymatically or chemically digested to generate a fructosyl amino acid or a fructosyl peptide, such as fructosyl valine, fructosyl valyl histidine and fructosyl hexapeptide, which in turn is quantified using a fructosyl amino acid oxidase disclosed herein. In this way, glycated albumin, HbA1c or fructosyl hexapeptide may be assayed. Accordingly, the kit for assaying glycated albumin, HbA1c or fructosyl hexapeptide may further contain a reagent for hydrolysis or protease in the above-mentioned kit for measurement of fructosyl valine or fructosyl valyl histidine.

In another aspect, an enzyme electrode having a fructosyl amino acid oxidase disclosed herein which is immobilized on the electrode is provided.

In another aspect, an enzyme sensor for assaying fructosyl valine, fructosyl valyl histidine, HbA1c or fructosyl hexapeptide includes the enzyme electrode described above as a working electrode.

The concentration of the fructosyl amino acid in a sample may be determined by measuring the amount of electrons generated by the enzyme reaction. Various sensor systems have been known in the art, including carbon electrode, metal electrode, and platinum electrode systems. A mutated fructosyl amino acid oxidase disclosed herein is immobilized on the electrodes. Non-limiting examples of the means for immobilization include cross-linking, encapsulation into a macromolecular matrix, coating with a dialysis membrane, an optical cross-linking polymer, an electroconductive polymer, an oxidation-reduction polymer, and any combination thereof.

When measurement is conducted in an amperometric system, a carbon electrode, gold electrode or platinum electrode provided with an immobilized enzyme is used as a working electrode, together with a counter electrode (such as a platinum electrode) and a reference electrode (such as an Ag/AgCl electrode). The electrodes are inserted into a buffer containing a mediator and kept at predetermined temperature. Predetermined voltage is applied to the working electrode, then a sample is added and increased value in electric current is measured. Non-limiting examples of the mediator which may be used in the assay include potassium ferricyanide, ferrocene, osmium derivative, ruthenium derivative, phenazine methosulfate, etc. It is generally also possible to use so-called two-electrode systems with one working electrode and one counter or pseudo-reference electrode.

Further, fructosyl amino acid may be assayed using an immobilized electron mediator in an amperometric system using a carbon electrode, gold electrode, or platinum electrode. The enzyme is immobilized on the electrode together with an electron mediator such as potassium ferricyanide, ferrocene, osmium derivative, or phenazine methosulfate in a macromolecular matrix by means of adsorption or covalent bonding to prepare a working electrode. It is inserted into buffer together with a counter electrode (such as a platinum electrode) and a reference electrode (such as an Ag/AgCl electrode), and kept at a predetermined temperature. Predetermined voltage is applied to the working electrode, then the sample is added and increased value in electric current is measured.

To prepare a sensor for the measurement of glycated albumin, HbA1c or fructosyl hexapeptide, the above-mentioned sensor for the measurement of fructosyl amino acid is further combined with a membrane containing immobilized proteinase (such as protease) to construct a complex sensor. The structure of such a complex sensor based on a continuous reaction by a combination of plural enzymes is well known in the art. See, for example, "Biosensor—Fundamental and Applications" by Anthony P. F. Tuner, Isao Karube and George S. Wilson, Oxford University Press, 1987.

The contents of all patents and reference documents cited in the present specification are entirely incorporated herein by reference.

EXAMPLES

The following examples are for illustration purposes and are not to be construed as limiting the invention disclosed in this document to only the embodiments disclosed in these examples.

Example 1

Preparation and Characterization of N1-1 FAOD Mutants

The study of structure-function relationship of Monomeric Sarcosine Oxidase (MSOX) revealed that the Proton Relay System (PRS) involved in transferring electrons from FAD to oxygen is comprised of Thr48 and Lys 265 with four $H_2O$ molecules (Trickey et al, Structure, 7, 331-345, 1999). The active site of fructosyl amino acid oxidase from *Pichia* sp. N1-1 strain (N-1-1 FAOD, SEQ ID NO: 2) has high homology with MSOX, especially in conserved residues which are predicted to be responsible for the Proton Relay System.

A predicted structural model of N1-1 FAOD (SEQ ID NO: 2) was constructed using the MSOX structure, and the amino acid residues Asn44, Ser46, Asn47, Lys48 and Lys269 were predicted to be involved in proton and electron transfer from FAD. Single or double mutations were introduced into those amino acid residues with the aim of modifying the electron acceptor availability of N1-1 FAOD (SEQ ID NO: 2).

Expression vectors of N1-1 FAOD (SEQ ID NO: 2) single mutants were created by site-directed mutagenesis using QuickChange® method from Stratagene Cloning Systems, La Jolla, Calif., with the N1-1 FAOD (SEQ ID NO: 2) wild type gene as a template. Primers were designed to introduce mutation at Asn44, Ser46, Asn47, Lys48 or Lys269. The amplified products were digested by Dpn I and transformed into *E. coli* DH5α and incubated in LB agar medium (50 µg/ml Kanamycin) at 37° C., overnight. The mutated sequences of the clones were verified with an ABI Prism BigDye Terminator cycle sequencing kit v3.0 on an ABI Prism 3130 Genetic Analyzer. Then, extracted plasmids were digested with Nco I and Sal I and ligated into the pET28(a) vector which was digested with Nco I and Sal I. *E. coli* BL21(DE3) cells transformed with the ligation mixtures were incubated in LB agar medium (50 µg/ml Kanamycin) at 37° C., overnight. Double mutants were created by combination of the primers using the same method.

*Escherichia coli* BL21 (DE3) cells harboring expression vectors of N1-1 FAOD (SEQ ID NO: 2) mutants were grown in 150 ml of LB medium containing 50 µg/ml kanamycin at 37° C. After reaching an A660 value of 0.6, 0.3 mM IPTG was added and incubated at 25° C. for an additional 5 hours. The cells were collected by centrifugation and washed twice with 0.85% NaCl.aq. Then, the cells were resuspended in 10 mM Potassium Phosphate Buffer (PPB) pH 7.0 and lysed by ultrasonic homogenizer. The lysate was centrifuged at 10,000×g, 4° C. for 10 min, and the supernatant was centrifuged at 50,000 rpm, 4° C. for 60 min, then the supernatant was dialyzed against 10 mM PPB (pH 7.0). The oxidase activity was assayed at 25° C. in 10 mM PPB, pH 7.0, 1.5 mM TODB, 2 U/ml horseradish peroxidase (POD), and 1.5 mM 4-aminoantipyrine (4AA) in the presence of substrates (0.2, 0.5, 0.75, 1, 2, 5 mM f-$^\alpha$Val or 5 mM). The formation of quinoneimine dye was measured spectrophotometrically at 546 nm. The dehydrogenase activity was assayed at 25° C. in 10 mM PPB (pH 7.0), 0.6 mM DCIP, and 6 mM methoxy PMS (mPMS) in the presence of substrates (0.2, 0.5, 1, 2, 5 mM f-$^\alpha$Val or 5 mM f-$^\alpha$Val-His).

In most cases, the oxidase activity was completely or substantially lost, but several mutants, such as N47A, S46A, K48A and N44A, showed relatively high activity. Among them, N47A showed the most remarkable feature. Although the oxidase activity of N47A decreased to about 20% of the wild type activity, the dehydrogenase activity of N47A remained more than 60% of the wild type activity. Consequently, N47A showed about 4 times higher dehydrogenase activity than oxidase activity. This characteristic of N47A may be desirable for use in a sensor strip employing fructosyl amino acid oxidase with an artificial electron acceptor. The kinetic parameters of crude preparations of wild type N1-1 FAOD (SEQ ID NO: 2) and N47A mutant are shown in Table 2.

TABLE 2

Kinetic parameters of crude preparation of N1-1 FAOD mutant and WT

| | 4AA/TODB/POD | | | mPMS/DCIP | | | |
| --- | --- | --- | --- | --- | --- | --- | --- |
| | $K_m$ (mM) | $V_{max}^A$ (U/mg) | $V_{max}/K_m$ | $K_m$ (mM) | $V_{max}^B$ (U/mg) | $V_{max}/K_m$ | B/A |
| WT | 2.64 | 0.71 | 0.26 | 3.22 | 0.60 | 0.190 | 1.2 |
| N47A | 1.42 | 0.11 | 0.07 | 9.13 | 0.82 | 0.09 | 7.5 |

Example 2

Purification of N1-1 Wild Type and N47A Mutant FAOD

The recombinant FAOD was purified as follows. First, a water-soluble fraction containing the enzyme was prepared from recombinant *Escherichia coli*. *E. coli* containing the expression vector was cultured in 7 L LB medium (37° C., in 10 L fermenter, 50 µg/ml ampicillin), then the expression was induced with IPTG (final concentration: 0.3 mM) at about $OD_{660}$=0.7 and culture temperature was lowered to 30° C. The cells were suspended in 100 mM PPb (pH 7.0) and disrupted four times using a French press. The supernatant liquid was subjected to ultracentrifugation (40,000 g, 90 minutes) and the supernatant was dialyzed against 10 mM PPb (pH 7.0) at 4° C. overnight to prepare a water-soluble fraction.

The water-soluble fraction was further subjected to a liquid chromatography to prepare a purified enzyme. The enzyme was further purified with an anion-exchange chromatography (DEAE-5PW). The water-soluble fraction was adsorbed to an anion-exchange chromatography column DEAE-5PW (5.0 mm I. D.×5 cm, Tosoh) equilibrated with 10 mM PPb (pH 7.0). After equilibration with 10 mM PPb (pH 7.0) in a 3-fold amount of the column volume, FAOD was eluted with 10 mM PPb (pH 7.0) containing 0.7 M of NaCl. The flow rate was set to 1 ml/min and eluate was collected every one minute. Absorption wavelength of 280 nm was used to monitor eluate.

The active fraction was separated using 35% ammonium sulfate and the supernatant liquid was subjected to hydrophobic chromatography. The active fraction was adsorbed to a hydrophobic chromatography column Resource Phe (1 ml, Pharmacia) equilibrated with 10 mM PPb (pH 6.5) containing 35% ammonium sulfate. After equilibration with 10 mM PPb (pH 6.5) containing 35% ammonium sulfate in a 3-fold amount of the column volume, FAOD was eluted with 10 mM PPb (pH 6.5). The flow rate was set to 2 ml/min and eluate was collected every one minute. The active fraction was separated with 45% ammonium sulfate, then the precipitate was dissolved in 10 mM PPb (pH 7.0) containing 1% mannose and 100 µM FAD and dialyzed against the same buffer at 4° C. for 6 hours. It was further dialyzed against 10 mM PPb (pH 8.0) containing 100 µM FAD at 4° C. for 6 hours. The dialyzed sample was used for the next anion-exchange chromatography.

The sample was adsorbed to an anion-exchange chromatography column Bioasit Q (4.6 mm. I. D.×5 cm, Tosoh) equilibrated with 10 mM PPb (pH 8.0). After equilibration with 10 mM PPb (pH 8.0) in a 3-fold amount of the column volume, FAOD was eluted with 10 mM PPb (pH 7.0) containing 0.3M NaCl. The flow rate was set to 1 ml/min and eluate was collected every one minute. The active fraction was dialyzed against 10 mM PPb (pH 7.0) at 4° C. overnight. Degree of purification of the sample was examined by SDS/PAGE. The sample was subjected to electrophoresis using Phast Gel 8-25, and the gel was stained with silver. Sample preparation, electrophoresis and staining was conducted in accordance with the manual attached to Phast System™ of GE Healthcare.

Figure 3:
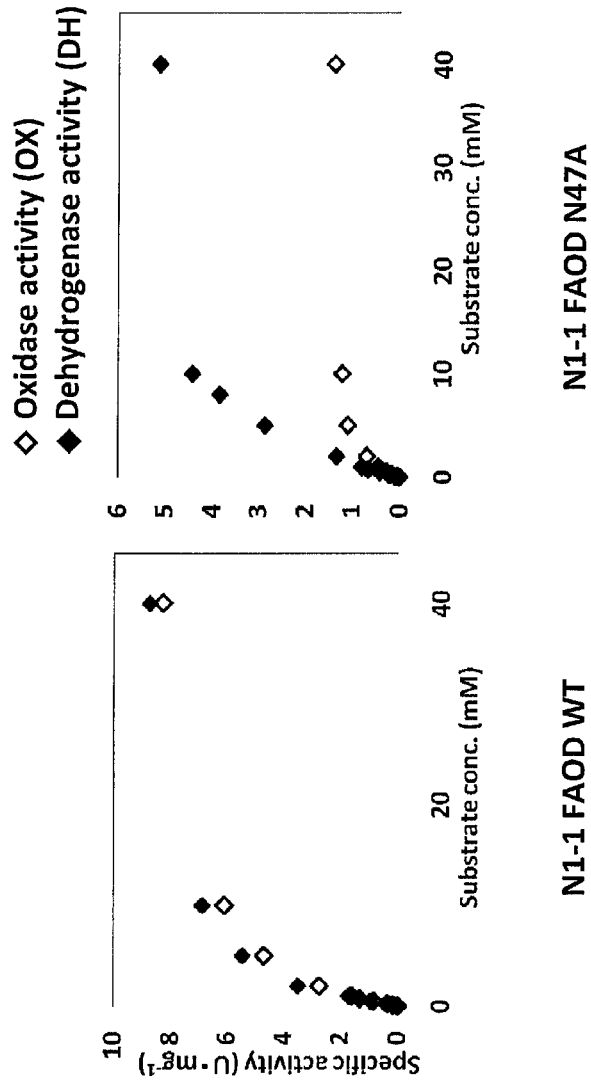
FIG. 3 shows the oxidase and dehydrogenase activity of purified N1-1 FAOD N47A mutant.

The oxidase and dehydrogenase activity of the purified enzymes were measured as in Example 1 and shown in FIG. 3. The kinetic parameters are shown in Table 3.

TABLE 3

Kinetic parameters of purified N1-1 FAOD WT (SEQ ID NO: 2) and mutant N47A

| | 4AA/TODB/POD | | | mPMS/DCIP | | | |
| --- | --- | --- | --- | --- | --- | --- | --- |
| | $K_m$ (mM) | $V_{max}^A$ (U/mg) | $V_{max}/K_m$ | $K_m$ (mM) | $V_{max}^B$ (U/mg) | $V_{max}/K_m$ | B/A |
| WT | 4.8 | 9.3 (100%) | 1.9 | 4.6 | 9.8 (100%) | 2.1 | 1.1 (100%) |
| N47A | 2.2 | 1.4 (15%) | 0.64 | 6.2 | 6.0 (61%) | 0.97 | 4.3 (391%) |

Example 3

Preparation of PnFPOX Mutants

Mutants derived from fructosyl amino acid oxidase from *Phaeosphaeria nolorum* (PnFPOX, SEQ ID NO: 1) were prepared and characterized.

Based on the alignment of N1-1 FAOD (SEQ ID NO: 2) and PnFPOX (SEQ ID NO: 1) (FIG. 1) and the results from Examples 1 and 2, Asn56 was predicted to be involved in proton and electron transfer from FAD. Various mutations were introduced into Asn56 with the aim of modifying the electron acceptor availability of the PnFAOD.

Mutations were introduced using site-directed mutagenesis as in Example 1, and BL21 (DE3) cells were transformed with an expression vector containing wild-type or mutant PnFPOX (SEQ ID NO: 1). The cultured cells were resuspended in 10 mM PPB, pH 7.0, and lysed by sonication. The lysate was centrifuged at 10,000 g at 4° C. for 20 min, and the supernatant was centrifuged at 50,000 rpm at 4° C. for 60 min. The oxidase and dehydrogenase activities were measured as in Example 1.

Activities of crude PnFPOX (SEQ ID NO: 1) wild-type and Asn56 variants are summarized in FIG. 4. Most Asn56 mutants showed drastic decreases in their oxidase activities (<20% of wild-type), except for Asn56Ser, which showed relatively high oxidase activity (41% of wild-type). Among them, some variants (Asn56Cys, Phe, Met, Val) showed relatively high dehydrogenase activities (>60% of wild-type), even higher than wild-type in Asn56Cys and Asn56Met. Kinetic parameters of Asn56 mutants are summarized in FIG. 5. Asn56Met and Asn56Val showed higher Vmax dehydrogenase (B)/Vmax oxidase (A) than Asn56Ala. Asn56Asp, Glu, and Pro lost both oxidase and dehydrogenase activities.

Example 4

Purification of PnFPOX N56A Mutant

BL21 (DE3) transformed with pEPN (pET28a-PnFPOX)-N56A was grown aerobically at 37° C. in LB medium (2 l) containing 50 µg kanamycin ml$^{-1}$. After reaching an A660 nm value of 0.6, the cells were induced with 0.3 mM IPTG, and the incubation was continued at 25° C. for 5.5 hours. The cells were harvested by centrifugation and resuspended in 10 mM PPB, pH 7.0, and lysed by 3 passages through a French press (1,000 kg cm$^{-2}$). The lysate was centrifuged at 10,000 g at 4° C. for 20 min, and the supernatant was centrifuged at 50,000 rpm at 4° C. for 60 min. The supernatant was then dialyzed against 10 mM PPB, pH 8.0, containing 25 µM FAD, and the crude enzyme solution was further purified.

Ammonium sulfate was added to the dialyzed supernatant to 35% saturation and then the precipitate formed was pelleted by centrifugation at 15,000 g for 20 min. The supernatant to which ammonium sulfate was added to 65% saturation was centrifuged at 15,000 g for 20 min. The resultant precipitate was dissolved in 10 mM PPB, pH 8.0, containing 25 µM FAD and 1% mannose and dialyzed at 4° C. against the same buffer, and subsequently dialyzed against 10 mM PPB, pH 8.0, containing 25 µM FAD. The dialyzed enzyme solution was applied to a RESOURCE Q column (GE Healthcare) equilibrated with 10 mM PPB, pH 8.0. The active flow-through fractions were collected, and adsorbed proteins that showed no FAOD activities were eluted with 1 M NaCl. The active flow-through fractions were collected and dialyzed against 10 mM PPB, pH 7.0. The dialyzed enzyme solution was applied to a HiLoad 16/60 Superdex 75 pg column (GE Healthcare) equilibrated with 10 mM PPB, pH 7.0. Gel filtration chromatography was carried out with the same buffer. The active fractions were collected, and the purified enzyme solution was dialyzed against 10 mM PPB, pH 7.0 containing 100 µM FAD, and stored at 4° C. The purity of the purified enzyme was confirmed by SDS-PAGE, and the concentration was measured using a DC Protein Assay Kit (Bio-Rad, CA, USA). The results are shown in Table 4.

TABLE 4

Purification of recombinant PnFPOX N56A

| Stage | Total activity (U) | Total Protein (mg) | Specific Activity (U/mg) | Purification (Fold) | Yield (%) |
|---|---|---|---|---|---|
| Soluble fraction | 95.4 | 566 | 0.17 | 1 | 100 |
| Ammonium Sulfate | 75.5 | 340 | 0.22 | 1.32 | 79 |
| Resource Q | 37.4 | 21.9 | 1.7 | 10.1 | 39 |
| HiLoad 1 | 23.7 | 5.12 | 4.6 | 27.5 | 25 |

Substrate was 1 mM f-αVal.

Figure 6:
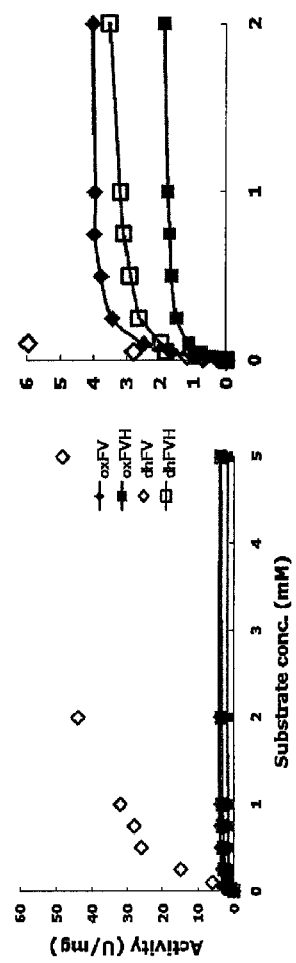
FIG. 6 shows the oxidase and dehydrogenase activity of purified PnFPOX N56A mutant.

The oxidase and dehydrogenase activities of the N56A mutant FAOD were measured. The SV curve and the kinetic parameters of the mutant FAOD are shown in FIG. 6 and Table 5, respectively. In FIG. 6, the left graph shows the activity in the substrate concentration of 0-5 mM, and the right graph is a magnified view for the substrate concentration of 0-2 mM. The N56A mutant showed significantly increased dehydrogenase activity toward both substrates.

TABLE 5

Kinetic parameters of purified PnFPOX N56A mutant

|  |  | 4AA/TODB/POD | | | mPMS/DCIP | |
|---|---|---|---|---|---|---|
| | Substrate | $K_m$ (mM) | $V_{max}$ (U/mg) | $V_{max}/K_m$ | $K_m$ (mM) | $V_{max}$ (U/mg) | $V_{max}/K_m$ |
| WT | f-αVal | 0.64 | 27.6 | 42.8 | 1.1 | 28.0 | 25 |
| | f-αValHis | 0.20 | 2.97 | 14.7 | — | — | — |
| N56A | f-αVal | 0.086 | 4.39 | 51.0 | 1.6 | 95.1 | 58.6 |
| | f-αValHis | 0.092 | 1.90 | 20.7 | 0.074 | 3.40 | 45.9 |

Example 5

Preparation and Characterization of Amadoriase II FAOD Mutants

Mutants derived from Amadoriase II (SEQ ID NO: 3) were prepared and characterized. Based on the alignment of N1-1 FAOD (SEQ ID NO: 2) and Amadoriase II (SEQ ID NO: 3) (FIG. 1) and the results from Examples 1-4, Asn52 was predicted to be involved in proton and electron transfer from FAD. A mutant having Asn52Ala mutation was prepared according to the method described in Example 1.

BL21 (DE3) cells were transformed with an expression vector containing Amadoriase II (SEQ ID NO: 3) wild-type or N52A mutant. The cultured cells were harvested and resuspended in 10 ml of 10 mM PPB, pH 7.0, and lysed by 2 passages through a French press (1,000 kg cm-2). The lysate was centrifuged at 10,000 g at 4° C. for 20 min, and the supernatant was centrifuged at 50,000 rpm at 4° C. for 60 min. The supernatant was then dialyzed against 10 mM PPB, pH 8.0, containing 25 μM FAD to prepare a crude enzyme solution. The crude preparation was purified by ammonium sulfate precipitation, anion exchange chromatography (RESOURCE™ Q column (GE Healthcare)), and gel filtration chromatography (HiLoad 16/60 Superdex 75 pg column (GE Healthcare)).

Figure 7:
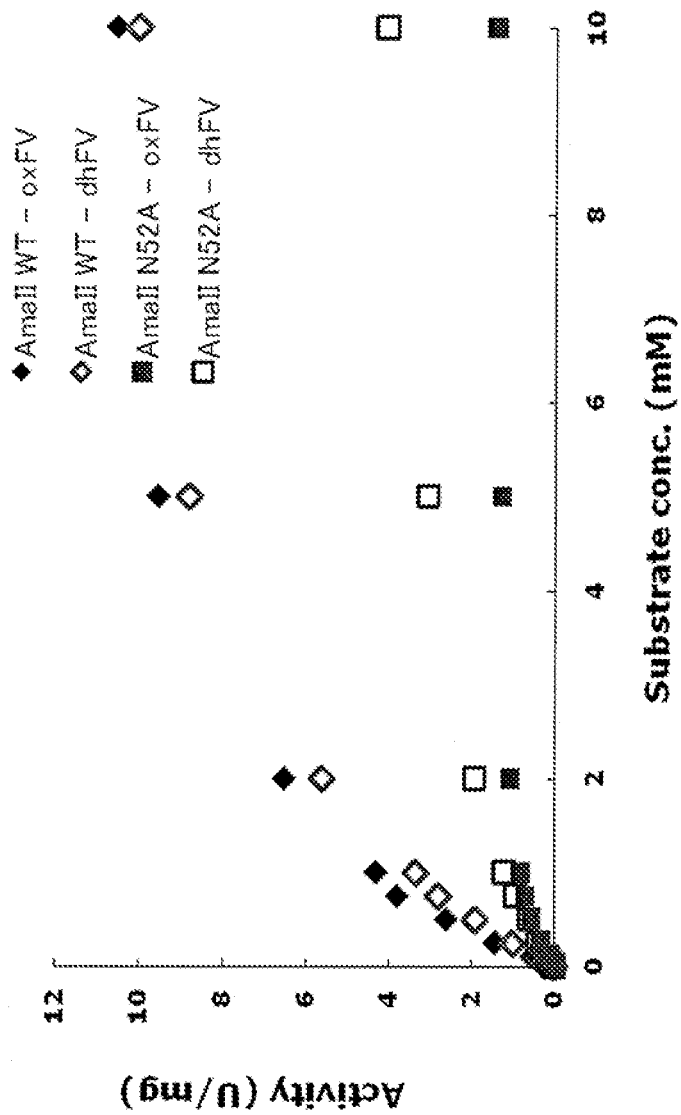
FIG. 7 shows the oxidase and dehydrogenase activity of purified Amadoriase II (SEQ ID NO: 3) wild type and N52A mutant.

The FAOD activity was assayed using 4AA/TODB/POD (oxidase activity) and PMS/DCIP (dehydrogenase activity) with f-αVal as a substrate. The results are shown in FIG. 7.

Kinetic parameters of purified Amadoriase II wild-type and Asn52Ala are summarized in FIG. 8. The mutant N52A showed about 2 times higher dehydrogenase activity than oxidase activity.

Example 6

Construction of Biosensor 40 mU/5 μl of either PnFPOX (SEQ ID NO: 1) wild type or N56A PnFPOX solution was mixed with 2% of AWP solution. 5 ul of the mixture was applied on a re-usable gold electrode (surface area: 7 mm$^2$) and dried up for 30 min at 30° C. The electrode was irradiated with UV-light for 1 min to prepare an electrode having the wild type or N56A PnFPOX immobilized. The electrode was immersed in a 2 ml PBS (pH 7.4) solution with 2 mM nitrosoaniline (NA; known from p. 33 ff. of International Patent Publication No. WO 2004/113900). Then, +200 mV vs Ag/AgCl was applied, and the current was monitored. When the steady state current was observed, sample solution containing different concentration of FV was added to the reaction mixture, and current increase was monitored. For measuring the enzyme activity in the absence of oxygen, Ar gas was continuously purged into reaction chamber.

Figure 9:
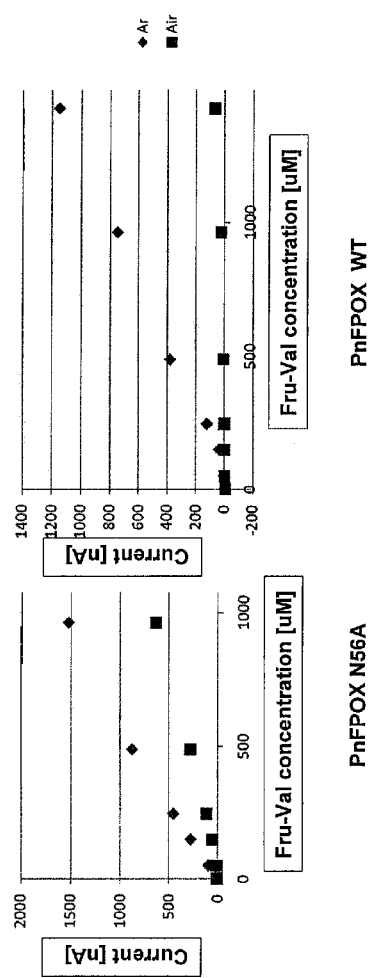
FIG. 9 shows assay of FV concentration using electrode having PnFPOX N56A or Wild type FAOD.

FIG. 9 shows the correlations between FV concentration and current increase of an electrode having PnFPOX N56A or Wild type enzyme, in the presence of oxygen or absence (under Ar gas). The effect of oxygen on the electrochemical reaction was observed, but the impact of the presence of oxygen was less than that for the Wild type. These results suggested that the activity of the fructosyl amino acid oxidase disclosed herein is less affected by the dissolved oxygen level.

Example 7

Preparation and Characterization of FPOX-C Mutant

A mutant derived from FPOX-C (SEQ ID NO: 7) having Asn52Ala mutation was prepared in the same manner as in Example 5. The crude enzyme preparation was used for enzyme activity assay without further purification. The FAOD activity was assayed using 4AA/TODB/POD (Ox: oxidase activity) and PMS/DCIP (DH: dehydrogenase activity) with either 1 mM f-αVal or 1 mM f-αVal-His as a substrate. The results are shown in Table 6 below.

TABLE 6

| | f-αVal | | f-αValHis | |
|---|---|---|---|---|
| | Ox (U/mg) | DH (U/mg) | Ox (U/mg) | DH (U/mg) |
| FPOX-C WT | 4.6 | 1.8 | 1.3 | 0.66 |
| FPO-C N56A | 0.53 | 4.3 | 0.49 | 1.7 |

The mutant FPOX-C N52A showed much higher dehydrogenase activity than oxidase activity toward both f-αVal and f-αVal-His.

Example 8

Preparation and Characterization of Loop Mutants

PnFPOX (SEQ ID NO: 1) shows oxidase activity toward fructosyl hexapeptide at a level of less 1% of the activity compared with FVH, whereas FPOX-C (SEQ ID NO: 7) shows no activity. On the other hand, FPOX-C (SEQ ID NO: 7) shows higher activity toward FVH than PnFPOX (SEQ ID NO: 1). From comparison of the amino acid sequence of both oxidases, significant difference between FAOD and FPOX is found in their loop regions.

Loop 1 Region
PnFPOX (SEQ ID NO: 1): (61) Val Ser Leu Arg Asn Pro Val Asp Leu Gln Leu Ala (72) (SEQ ID NO: 13)
FPOX-C (SEQ ID NO: 7): (61) Ile Arg Leu Arg Asn Lys Val Asp Leu Gln Met Ser (72) (SEQ ID NO: 14)
Loop 2 Region
PnFPOX (SEQ ID NO: 1): (109) Ser Gly Tyr Gln Ala Leu Val Asp Ala Gly Leu Asp Ala Thr Asn Glu (124) (SEQ ID NO: 15)
FPOX-C (SEQ ID NO: 7): (109) Lys Gln Tyr Gln Ala Leu His Asp Ala Gly Ala Gly Leu Glu Lys Thr His Ala (126) (SEQ ID NO: 16)

At the loop 1 region (12aa) 5 amino acid residues are different between PnFPOX (SEQ ID NO: 1) and FPOX-C (SEQ ID NO: 7). At the loop 2 region (16aa), 2 amino acid insertions and 7 amino acid substitutions are observed.

Chimeric loop mutants where loop regions of 1 PnFPOX (SEQ ID NO: 1) and FPOX-C (SEQ ID NO: 7) are exchanged for each other, as well as N56A mutants thereof were prepared. Based on the partial amino acid sequences shown above, 8 types of mutants were prepared:

(i) PnFPOX/L1ExC (i.e., PnFPOX (SEQ ID NO: 1) where loop 1 region (SEQ ID NO: 13) is substituted with the loop 1 region (SEQ ID NO: 14) from FPOX-C (SEQ ID NO: 2))

(ii) PnFPOX/L1ExC/N56A (i.e., N56A mutant of PnFPOX (SEQ ID NO: 1) where loop 1 region (SEQ ID NO: 13) is substituted with the loop 1 region (SEQ ID NO: 14) from FPOX-C (SEQ ID NO: 7))

(iii) PnFPOX/L2ExC (i.e., PnFPOX (SEQ ID NO: 1) where loop 2 region (SEQ ID NO: 15) is substituted with the loop 2 region (SEQ ID NO: 16) from FPOX-C(SEQ ID NO: 2))

(iv) PnFPOX/L2ExC/N56A (i.e., N56 A mutant of PnFPOX (SEQ ID NO: 1) where loop 2 region (SEQ ID NO: 15) is substituted with the loop 2 region (SEQ ID NO: 16) from FPOX-C(SEQ ID NO: 7))

(v) FPOX-C/L1ExPn (i.e., FPOX-C (SEQ ID NO: 7) where loop 1 region (SEQ ID NO: 14) is substituted with the loop 1 region (SEQ ID NO: 13) from PnFPOX (SEQ ID NO: 1))

(vi) FPOX-C/L1ExPn/N56A (i.e., N56 A mutant of FPOX-C (SEQ ID NO: 7) where loop 1 region (SEQ ID NO: 14) is substituted with the loop 1 region (SEQ ID NO: 13) from PnFPOX (SEQ ID NO: 1))

(vii) FPOX-C/L2ExPn (i.e., FPOX-C (SEQ ID NO: 7) where loop 2 region (SEQ ID NO: 16) is substituted with the loop 2 region (SEQ ID NO: 15) from PnFPOX (SEQ ID NO: 1))

(viii) FPOX-C/L2ExPn/N56A (i.e., N56A mutant of FPOX-C (SEQ ID NO: 7) where loop 2 region (SEQ ID NO: 16) is substituted with the loop 2 region (SEQ ID NO: 15) from PnFPOX (SEQ ID NO: 1)).

Introduction of mutations and preparation of crude enzymes were carried out as described in Examples 1 and 5. The FAOD activity was assayed using 4AA/TODB/POD (Ox: oxidase activity) and PMS/DCIP (DH: dehydrogenase activity) with either 1 mM f-αVal, 1 mM f-αVal-His or 5 mM fructosyl hexapeptide (F—HP) as a substrate.

Both PnFPOX/L1ExC and PnFPOX/L2ExC showed higher oxidation activity toward f-αVal-His compared with wild type PnFPOX. FPOX-C/L1ExPn showed the activity toward F—HP which was not observed in the wild type FPOX-C. Interestingly, PnFPOX/L2ExC showed increased activity toward F—HP, while PnFPOX/L1ExC almost lost the activity toward F—HP. These results indicated that the improvement of the PnFPOX activity toward F—HP could be further improved by modification of the loop region.

Introduction of the N56A mutation into these loop mutants resulted in decreased oxidase activity and increased dehydrogenase activity. Both PnFPOX/L1ExC/N56A and PnFPOX/L2ExC/N56A showed higher dehydrogenase activity compared with their oxidase activity toward f-αVal. The dehydrogenase activity toward f-αVal of PnFPOX/L2ExC/N56A showed marked increase compared with PnFPOX/N56A, and it was higher than those of FPOX-C/N56A.

Both PnFPOX/L1ExC/N56A and PnFPOX/L2ExC/N56A showed the higher dehydrogenase activity toward f-αVal-His compared with their oxidase activity. The highest dehydrogenase activity was observed in PnFPOX/L2ExC/N56A, which is almost similar with those of FPOX-C/N56A.

Representative results are shown in Table 7 below.

TABLE 7

| | | f-αVal | | f-αVal-His | | F-HP |
|---|---|---|---|---|---|---|
| | | Ox (U/mg) | DH (U/mg) | Ox (U/mg) | DH (U/mg) | Ox (mU/mg) |
| P.n FPOX | WT | 1.3 | 1.1 | 0.11 | 0.065 | 0.45 |
| | N56A | 0.14 | 1.5 | 0.058 | 0.14 | — |
| | L2ExC | 3 | 2.6 | 0.41 | 0.37 | 1.4 |
| | L2ExC/N56A | 0.55 | 4.2 | 0.23 | 0.61 | — |
| FPOX-C | L1ExPn | 2.4 | 3.1 | 0.78 | 0.85 | 4.5 |
| | L1ExPn/N56A | 0.31 | 6.5 | 0.26 | 2.2 | — |

In one non-limiting application, the mutated fructosyl amino acid oxidases disclosed herein may be used for the measurement of glycated proteins, such as hemoglobin (HbA1c) which is clinically useful in diagnosis and control of diabetic conditions. Still, it should be appreciated that alternative applications and uses for the mutated fructosyl amino acid oxidases disclosed herein are also contemplated.

Although embodiments of the invention have been described using specific terms, such description is for illustrative purposes only, and it is to be understood that changes and variations obvious to the skilled artisan are to be considered within the scope of the claims that follow and their equivalents.

What is claimed is:

1. A mutant fructosyl amino acid oxidase, comprising a modification at a position corresponding to position 56 of the amino acid sequence set forth in SEQ ID NO: 1, wherein the modification includes a substitution of the amino acid residue Asn with an amino acid residue selected from Ala, Cys, Phe, Met and Val.

2. The mutant fructosyl amino acid oxidase of claim 1, which includes a reduced oxidase activity as compared to the wild-type fructosyl amino acid oxidase, and an increased dehydrogenase activity compared to the wild-type fructosyl amino acid oxidase.

3. The mutant fructosyl amino acid oxidase of claim 1, which includes an oxidase activity of 30% or less of that of the wild-type fructosyl amino acid oxidase, and a dehydrogenase activity of 50% or more of the wild-type fructosyl amino acid oxidase.

4. The mutant fructosyl amino acid oxidase of claim 1, which includes an increased dehydrogenase activity compared to the wild-type fructosyl amino acid oxidase.

5. The mutant fructosyl amino acid oxidase of claim 1, comprising an amino acid sequence selected from the group consisting of SEQ ID NOs: 1-12 wherein the amino acid residue Asn at a position corresponding to the position 56 of the amino acid sequence set forth in SEQ ID NO: 1 is substituted with an amino acid residue selected from Ala, Cys, Phe, Met and Val.

6. The mutant fructosyl amino acid oxidase of claim 1, which includes the amino acid sequence set forth in SEQ ID NO: 1 wherein the amino acid residue Asn at the position 56 is substituted with an amino acid residue selected from Ala, Cys, Phe, Met and Val.

7. The mutant fructosyl amino acid oxidase of claim 6, wherein the amino acid residues Ser Gly Tyr Gln Ala Leu Val Asp Ala Gly Leu Asp Ala Thr Asn Glu at positions 109-124 of SEQ ID NO: 1 are replaced with the sequence: Lys Gln Tyr Gln Ala Leu His Asp Ala Gly Ala Gly Leu Glu Lys Thr His Ala of SEQ ID NO: 16.

8. The mutant fructosyl amino acid oxidase of claim 1, which includes the amino acid sequence set forth in SEQ ID NO: 2 wherein the amino acid residue Asn at position 47 is substituted with an amino acid residue selected from Ala, Cys, Phe, Met and Val.

9. The mutant fructosyl amino acid oxidase of claim 1, which includes the amino acid sequence set forth in SEQ ID NO: 3 wherein the amino acid residue Asn at position 52 is substituted with an amino acid residue selected from Ala, Cys, Phe, Met and Val.

10. The mutant fructosyl amino acid oxidase of claim 1, which includes the amino acid sequence set forth in SEQ ID NO: 7 wherein the amino acid residue Asn at the position 56 is substituted with an amino acid residue selected from Ala, Cys, Phe, Met and Val.

11. The mutant fructosyl amino acid oxidase of claim 10, wherein the amino acid residues Ile Arg Leu Arg Asn Lys Val Asp Leu Gln Met Ser at positions 61-72 of SEQ ID NO: 7 are replaced with the sequence Val Ser Leu Arg Asn Pro Val Asp Leu Gln Leu Ala of SEQ ID NO: 13.

12. A mutant fructosyl amino acid oxidase, comprising the amino acid sequence set forth in SEQ ID NO: 1 wherein the amino acid residues Val Ser Leu Arg Asn Pro Val Asp Leu Gln Leu Ala at positions 61-72 of SEQ ID NO: 1 are replaced with the sequence: Ile Arg Leu Arg Asn Lys Val Asp Leu Gln Met Ser of SEQ ID NO: 14.

13. A mutant fructosyl amino acid oxidase, comprising the amino acid sequence set forth in SEQ ID NO: 1 wherein the amino acid residues Ser Gly Tyr Gln Ala Leu Val Asp Ala Gly Leu Asp Ala Thr Asn Glu at positions 109-124 of SEQ ID NO: 1 are replaced with the sequence: Lys Gln Tyr Gln Ala Leu His Asp Ala Gly Ala Gly Leu Glu Lys Thr His Ala of SEQ ID NO: 16.

14. A method for assaying a glycated protein in a sample, comprising contacting the sample with the fructosyl amino acid oxidase of claim 1, and measuring the amount of the glycated protein oxidized by the fructosyl amino acid oxidase.

15. A method for assaying HbA1c, comprising digesting HbA1c in a sample to generate fructosyl valine or fructosyl valyl histidine, contacting the fructosyl valine or fructosyl valyl histidine with the fructosyl amino acid oxidase of claim 1, and measuring the amount of oxidized fructosyl valine or fructosyl valyl histidine.

16. A device for assaying fructosyl valine, fructosyl valyl histidine, HbA1c or fructosyl hexapeptide in a sample, comprising the fructosyl amino acid oxidase of claim 1 and an electron transfer mediator.

17. A kit for assaying fructosyl valine, fructosyl valyl histidine, HbA1c or fructosyl hexapeptide in a sample, comprising the fructosyl amino acid oxidase of claim 1 and an electron transfer mediator.

18. An enzyme electrode, comprising the fructosyl amino acid oxidase of claim 1 which is immobilized on the electrode.

19. An enzyme sensor for assaying fructosyl valine, fructosyl valyl histidine, HbA1c or fructosyl hexapeptide, comprising the enzyme electrode of claim 18 as a working electrode.

* * * * *

SEQUENCE LISTING

<160> NUMBER OF SEQ ID NOS: 16

<210> SEQ ID NO 1
<211> LENGTH: 437
<212> TYPE: PRT
<213> ORGANISM: Phaeosphaeria nodorum

<400> SEQUENCE: 1

-continued

```
Met Ala Pro Ser Arg Ala Asn Thr Ser Val Ile Val Gly Gly Gly
 1               5                  10                  15
Gly Thr Ile Gly Ser Ser Thr Ala Leu His Leu Val Arg Ser Gly Tyr
                20                  25                  30
Thr Pro Ser Asn Val Thr Val Leu Asp Ala Tyr Pro Ile Pro Ser Ser
            35                  40                  45
Gln Ser Ala Gly Asn Asp Leu Asn Lys Ile Met Gly Val Ser Leu Arg
        50                  55                  60
Asn Pro Val Asp Leu Gln Leu Ala Leu Glu Ala Arg Gln Met Trp Asn
 65                 70                  75                  80
Glu Asp Glu Leu Phe Lys Lys Phe Phe His Asn Thr Gly Arg Leu Asp
                85                  90                  95
Cys Ala His Gly Glu Lys Asp Ile Ala Asp Leu Lys Ser Gly Tyr Gln
                100                 105                 110
Ala Leu Val Asp Ala Gly Leu Asp Ala Thr Asn Glu Trp Leu Asp Ser
                115                 120                 125
Glu Asp Glu Ile Leu Lys Arg Met Pro Leu Leu Ser Arg Asp Gln Ile
                130                 135                 140
Lys Gly Trp Lys Ala Ile Phe Ser Lys Asp Gly Gly Trp Leu Ala Ala
145                 150                 155                 160
Ala Lys Ala Ile Asn Ala Val Gly Glu Tyr Leu Arg Asp Gln Gly Val
                165                 170                 175
Arg Phe Gly Phe Tyr Gly Ala Gly Ser Phe Lys Ala Pro Leu Leu Ala
                180                 185                 190
Glu Gly Val Cys Ile Gly Val Glu Thr Val Asp Gly Thr Arg Tyr Tyr
                195                 200                 205
Ala Asp Lys Val Val Leu Ala Ala Gly Ala Trp Ser Pro Thr Leu Val
            210                 215                 220
Glu Leu His Glu Gln Cys Val Ser Lys Ala Trp Val Tyr Gly His Ile
225                 230                 235                 240
Gln Leu Thr Pro Glu Glu Ala Ala Arg Tyr Lys Asn Ser Pro Val Val
                245                 250                 255
Tyr Asn Gly Asp Val Gly Phe Phe Phe Glu Pro Asn Glu His Gly Val
                260                 265                 270
Ile Lys Val Cys Asp Glu Phe Pro Gly Phe Thr Arg Phe Lys Met His
            275                 280                 285
Gln Pro Phe Gly Ala Lys Ala Pro Lys Arg Ile Ser Val Pro Arg Ser
            290                 295                 300
His Ala Lys His Pro Thr Asp Thr Ile Pro Asp Ala Ser Asp Val Ser
305                 310                 315                 320
Ile Arg Arg Ala Ile Ala Thr Phe Met Pro Gln Phe Lys Asn Lys Lys
                325                 330                 335
Met Phe Asn Gln Ala Met Cys Trp Cys Thr Asp Thr Ala Asp Ala Ala
                340                 345                 350
Leu Leu Ile Cys Glu His Pro Glu Trp Lys Asn Phe Val Leu Ala Thr
            355                 360                 365
Gly Asp Ser Gly His Ser Phe Lys Leu Leu Pro Asn Ile Gly Lys His
            370                 375                 380
Val Val Glu Leu Leu Glu Gly Thr Leu Ala Asp Asp Leu Ala His Ala
385                 390                 395                 400
Trp Arg Trp Arg Pro Gly Ser Gly Asp Ala Leu Lys Ser Arg Arg Ser
                405                 410                 415
Ala Pro Ala Lys Asp Leu Ala Asp Met Pro Gly Trp Asn His Asp Lys
                420                 425                 430
```

```
Pro Arg Ala Asn Leu
        435

<210> SEQ ID NO 2
<211> LENGTH: 427
<212> TYPE: PRT
<213> ORGANISM: Pichia spec.

<400> SEQUENCE: 2

Met Glu Ser Ile Ile Ile Val Gly Ala Gly Thr Phe Gly Leu Ser Thr
1               5                   10                  15

Ala Leu Gln Leu Ala Arg Asp Gly Tyr Lys Asn Ile Lys Cys Phe Asp
            20                  25                  30

Lys Phe Pro Val Pro Ser Glu Ile Ala Ala Gly Asn Asp Ser Asn Lys
        35                  40                  45

Ile Phe His Tyr Asp Tyr Val Ala Pro Leu Ala Lys Pro Asn Ser Lys
    50                  55                  60

Glu Arg Leu Ser Leu Glu Ala Leu His Leu Trp Lys Thr Asp Pro Val
65                  70                  75                  80

Tyr Lys Pro Tyr Tyr His Pro Val Gly Phe Ile Leu Ala Ala Ser Ser
                85                  90                  95

Asp Ala Pro Leu Leu His Asp Lys Glu Tyr Tyr Glu Glu Leu Gln Lys
            100                 105                 110

Asn Gly Leu Arg Asn Tyr Arg Tyr Ile Ser Thr Pro Glu Glu Phe Arg
        115                 120                 125

Glu Tyr Leu Pro Ile Leu Lys Gly Pro Leu Pro Asn Trp Arg Gly Tyr
    130                 135                 140

Val Leu Asp Gly Asp Asn Gly Trp Leu His Ala Arg Asp Ser Leu Lys
145                 150                 155                 160

Ser Ala Tyr Glu Glu Cys Lys Arg Leu Gly Val Glu Phe Val Phe Gly
                165                 170                 175

Asp Asp Gly Glu Ile Val Glu Leu Leu Asn Glu Asn Gly Lys Leu Thr
            180                 185                 190

Gly Ile Arg Ala Arg Ser Gly Ala Ile Phe Ser Ala Gln Lys Tyr Val
        195                 200                 205

Leu Ser Ser Gly Ala Asn Ala Val Thr Leu Leu Asn Phe Gln Arg Gln
    210                 215                 220

Leu Glu Gly Lys Cys Phe Thr Leu Ala His Phe Lys Val Thr Asp Glu
225                 230                 235                 240

Glu Ala Lys Ala Phe Lys Ser Leu Pro Val Leu Phe Asn Ala Glu Lys
                245                 250                 255

Gly Phe Phe Glu Ala Asp Glu Asn Asn Glu Ile Lys Ile Cys Asn
            260                 265                 270

Glu Tyr Pro Gly Phe Thr His Thr Asn Glu Ser Gly Glu Ser Ile Pro
        275                 280                 285

Leu Tyr Arg Met Glu Ile Pro Leu Glu Ser Ala Leu Glu Ile Arg Gln
    290                 295                 300

Tyr Leu Lys Glu Thr Met Pro Gln Phe Ala Asp Arg Pro Phe Thr Lys
305                 310                 315                 320

Thr Arg Ile Cys Trp Cys Thr Asp Ser Pro Asp Met Gln Leu Ile Leu
                325                 330                 335

Cys Thr His Pro Glu Tyr Thr Asn Leu Ile Val Ala Ser Gly Asp Ser
            340                 345                 350

Gly Asn Ser Phe Lys Ile Met Pro Ile Ile Gly Lys Tyr Val Ser Lys
        355                 360                 365
```

-continued

```
Val Val Thr Lys Gly Asp Lys Gly Leu Asp Pro Glu Asp Lys Glu Cys
    370             375                 380

Trp Lys Trp Arg Pro Glu Thr Trp Asp Lys Arg Gly Gln Val Arg Trp
385             390                 395                 400

Gly Gly Arg Tyr Arg Val Ala Asp Leu Asn Glu Ile Glu Glu Trp Val
            405                 410                 415

Ser Val Glu Asn Pro Thr Pro His Lys Leu Glu
        420                 425

<210> SEQ ID NO 3
<211> LENGTH: 438
<212> TYPE: PRT
<213> ORGANISM: Aspergillus fumigatus

<400> SEQUENCE: 3

Met Ala Val Thr Lys Ser Ser Leu Leu Ile Val Gly Ala Gly Thr
1               5                   10                  15

Trp Gly Thr Ser Thr Ala Leu His Leu Ala Arg Arg Gly Tyr Thr Asn
            20                  25                  30

Val Thr Val Leu Asp Pro Tyr Pro Val Pro Ser Ala Ile Ser Ala Gly
            35                  40                  45

Asn Asp Val Asn Lys Val Ile Ser Ser Gly Gln Tyr Ser Asn Asn Lys
    50                  55                  60

Asp Glu Ile Glu Val Asn Gly Ile Leu Ala Glu Ala Phe Asn Gly
65                  70                  75                  80

Trp Lys Asn Asp Pro Leu Phe Lys Pro Tyr Tyr His Thr Gly Leu
                85                  90                  95

Leu Met Ser Ala Cys Ser Gln Glu Gly Leu Asp Arg Leu Gly Val Arg
            100                 105                 110

Val Arg Pro Gly Glu Asp Pro Asn Leu Val Glu Leu Thr Arg Pro Glu
            115                 120                 125

Gln Phe Arg Lys Leu Ala Pro Glu Gly Val Leu Gln Gly Asp Phe Pro
    130                 135                 140

Gly Trp Lys Gly Tyr Phe Ala Arg Ser Gly Ala Gly Trp Ala His Ala
145                 150                 155                 160

Arg Asn Ala Leu Val Ala Ala Arg Glu Ala Gln Arg Met Gly Val
                165                 170                 175

Lys Phe Val Thr Gly Thr Pro Gln Gly Arg Val Val Thr Leu Ile Phe
            180                 185                 190

Glu Asn Asn Asp Val Lys Gly Ala Val Thr Gly Asp Gly Lys Ile Trp
    195                 200                 205

Arg Ala Glu Arg Thr Phe Leu Cys Ala Gly Ala Ser Ala Gly Gln Phe
210                 215                 220

Leu Asp Phe Lys Asn Gln Leu Arg Pro Thr Ala Trp Thr Leu Val His
225                 230                 235                 240

Ile Ala Leu Lys Pro Glu Glu Arg Ala Leu Tyr Lys Asn Ile Pro Val
                245                 250                 255

Ile Phe Asn Ile Glu Arg Gly Phe Phe Phe Glu Pro Asp Glu Glu Arg
            260                 265                 270

Gly Glu Ile Lys Ile Cys Asp Glu His Pro Gly Tyr Thr Asn Met Val
    275                 280                 285

Gln Ser Ala Asp Gly Thr Met Met Ser Ile Pro Phe Glu Lys Thr Gln
    290                 295                 300

Ile Pro Lys Glu Ala Glu Thr Arg Val Arg Ala Leu Leu Lys Glu Thr
305                 310                 315                 320
```

```
Met Pro Gln Leu Ala Asp Arg Pro Phe Ser Phe Ala Arg Ile Cys Trp
                325                 330                 335

Cys Ala Asp Thr Ala Asn Arg Glu Phe Leu Ile Asp Arg His Pro Gln
            340                 345                 350

Tyr His Ser Leu Val Leu Gly Cys Gly Ala Ser Gly Arg Gly Phe Lys
        355                 360                 365

Tyr Leu Pro Ser Ile Gly Asn Leu Ile Val Asp Ala Met Glu Gly Lys
    370                 375                 380

Val Pro Gln Lys Ile His Glu Leu Ile Lys Trp Asn Pro Asp Ile Ala
385                 390                 395                 400

Ala Asn Arg Asn Trp Arg Asp Thr Leu Gly Arg Phe Gly Gly Pro Asn
                405                 410                 415

Arg Val Met Asp Phe His Asp Val Lys Glu Trp Thr Asn Val Gln Tyr
            420                 425                 430

Arg Asp Ile Ser Lys Leu
        435

<210> SEQ ID NO 4
<211> LENGTH: 437
<212> TYPE: PRT
<213> ORGANISM: Penicillium janthinellum

<400> SEQUENCE: 4

Met Ala His Ser Arg Glu Ser Thr Lys Ile Val Ile Gly Gly Gly
1                 5                  10                  15

Gly Thr Met Gly Ser Ser Thr Ala Leu His Leu Ile Arg Ser Gly Tyr
                20                  25                  30

Thr Pro Ser Asn Ile Thr Val Leu Asp Val Tyr Pro Ile Pro Ser Leu
            35                  40                  45

Gln Ser Ala Gly Tyr Asp Leu Asn Lys Ile Met Ser Ile Arg Leu Arg
        50                  55                  60

Asn Gly Pro Asp Leu Gln Leu Ser Leu Glu Ala Leu Asp Met Trp Lys
65                  70                  75                  80

Asn Asp Pro Leu Phe Lys Pro Phe Phe His Asn Val Gly Met Leu Asp
                85                  90                  95

Cys Ser Ser Ser Gln Glu Gly Ile Ala Ser Leu Arg Arg Lys His Gln
            100                 105                 110

Asp Leu Ile Asp Ala Asn Ile Gly Leu Glu Lys Thr Asn Ile Trp Leu
        115                 120                 125

Glu Ser Glu Asp Asp Ile Leu Ala Lys Ala Pro His Phe Thr Arg Glu
    130                 135                 140

Gln Ile Lys Gly Trp Lys Gly Leu Phe Cys Gly Asp Gly Gly Trp Leu
145                 150                 155                 160

Ala Ala Ala Lys Ala Ile Asn Ala Ile Gly Thr Phe Leu Lys Ser Gln
                165                 170                 175

Gly Val Lys Phe Gly Phe Gly Ser Ala Gly Thr Phe Lys Arg Pro Leu
            180                 185                 190

Phe Ala Pro Asp Gly Ala Thr Cys Ser Gly Val Glu Thr Val Asp Gly
        195                 200                 205

Thr Lys Tyr Phe Ala Asp Lys Val Val Leu Ala Ala Gly Ala Trp Ser
    210                 215                 220

Ser Thr Leu Val Asp Leu Glu Asp Gln Cys Val Ser Lys Ala Trp Val
225                 230                 235                 240

Phe Ala His Ile Gln Leu Thr Pro Gln Glu Ser Ala Gln Tyr Lys Asp
                245                 250                 255
```

```
Val Pro Val Val Tyr Asp Gly Asp Tyr Gly Phe Phe Glu Pro Asn
        260                 265                 270

Glu His Gly Val Ile Lys Val Cys Asp Glu Phe Pro Gly Phe Ser Arg
            275                 280                 285

Phe Lys Leu His Gln Pro Tyr Gly Ala Thr Ser Pro Lys Leu Ile Ser
    290                 295                 300

Val Pro Arg Ser His Ala Lys His Pro Thr Asp Thr Tyr Pro Asp Ser
305                 310                 315                 320

Ser Glu Glu Thr Ile Arg Lys Ala Ile Ala Arg Phe Met Pro Arg Phe
                325                 330                 335

Lys Asp Lys Glu Leu Phe Asn Arg Ser Met Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Val Leu Pro Asn
    370                 375                 380

Ile Gly Lys His Val Val Glu Leu Ile Glu Gly Arg Leu Pro Gln Asp
385                 390                 395                 400

Leu Ala Gly Ala Trp Arg Trp Arg Pro Gly Gly Asp Ala Leu Lys Ser
                405                 410                 415

Lys Arg Ser Ala Pro Ala Lys Asp Leu Ala Glu Met Pro Gly Trp Lys
            420                 425                 430

His Asp Ala Lys Leu
            435

<210> SEQ ID NO 5
<211> LENGTH: 441
<212> TYPE: PRT
<213> ORGANISM: Ulocladium spec.

<400> SEQUENCE: 5

Met Ala Pro Asn Arg Ala Asn Ile Ser Val Ile Val Gly Gly Gly
1               5                   10                  15

Gly Thr Ile Gly Ser Ser Thr Ala Leu His Leu Val Arg Ser Gly Tyr
                20                  25                  30

Thr Pro Ser Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
        50                  55                  60

Asn Lys Val Asp Leu Gln Leu Ser Leu Glu Ala Arg Gln Met Trp Thr
65                  70                  75                  80

Glu Asp Asp Leu Phe Lys Glu Tyr Phe His Lys Thr Gly Arg Leu Asp
                85                  90                  95

Cys Ala His Gly Glu Lys Gly Leu Ala Asp Leu Lys Gln Ala Tyr Gln
            100                 105                 110

Ala Leu Leu Asp Ala Asn Ala Gly Leu Glu Ala Thr Thr Glu Trp Leu
        115                 120                 125

Asp Ser Glu Asp Lys Ile Leu Glu Lys Met Pro Leu Leu Asn Arg Asp
    130                 135                 140

Gln Ile Lys Gly Trp Lys Ala Val Phe Ser Glu Asp Gly Gly Trp Leu
145                 150                 155                 160

Ala Ala Ala Lys Ala Ile Asn Ala Ile Gly Arg Phe Leu Arg Asp Gln
                165                 170                 175

Gly Val Lys Phe Gly Phe Gly Ala Gly Ser Phe Lys Gln Pro Leu
            180                 185                 190
```

```
Leu Ala Glu Gly Val Cys Val Gly Val Glu Thr Val Asp Gly Thr Arg
            195                 200                 205

Tyr Tyr Ala Asp Lys Val Val Leu Ala Ala Gly Ala Trp Ser Pro Ala
        210                 215                 220

Leu Val Asp Leu Gln Asp Gln Cys Val Ser Lys Ala Trp Val Tyr Ala
225                 230                 235                 240

His Ile Gln Leu Ser Pro Ser Glu Ala Ala Glu Tyr Lys Asn Val Pro
            245                 250                 255

Val Val Tyr Asn Gly Asp Val Gly Phe Phe Phe Glu Pro Asp Glu Tyr
        260                 265                 270

Gly Val Ile Lys Val Cys Asp Glu Phe Pro Gly Phe Thr Arg Phe Lys
            275                 280                 285

Gln His Gln Pro Phe Gly Ala Ser Ala Pro Lys Arg Ile Ser Val Pro
        290                 295                 300

Arg Ser Ala Ala Lys His Pro Thr Asp Thr Tyr Pro Asp Ala Ser Glu
305                 310                 315                 320

Val Ser Ile Arg Lys Ala Ile Ala Thr Phe Leu Pro Lys Phe Thr Glu
            325                 330                 335

Lys Glu Val Phe Asn Arg His Leu Cys Trp Cys Thr Asp Thr Ala Asp
            340                 345                 350

Ala Ala Leu Leu Met Cys Glu His Pro Glu Trp Lys Asn Phe Val Leu
        355                 360                 365

Ala Thr Gly Asp Ser Gly His Thr Phe Lys Leu Leu Pro Asn Ile Gly
        370                 375                 380

Lys His Val Val Glu Leu Leu Glu Gly Thr Leu Ala Asp Asp Leu Ala
385                 390                 395                 400

His Ala Trp Arg Trp Arg Pro Gly Thr Gly Asp Ala Leu Lys Ser Arg
            405                 410                 415

Arg Ala Ala Arg Ala Lys Asp Leu Ala Asp Met Pro Gly Trp Asn His
        420                 425                 430

Asp Gly Glu Ala Pro Arg Ala Lys Leu
        435                 440

<210> SEQ ID NO 6
<211> LENGTH: 437
<212> TYPE: PRT
<213> ORGANISM: Eupenicillium terrenum

<400> SEQUENCE: 6

Met Ala His Ser Arg Ala Ser Thr Lys Val Val Val Gly Gly Gly
1               5                   10                  15

Gly Thr Ile Gly Ser Ser Thr Ala Leu His Leu Ile Arg Ser Gly Tyr
            20                  25                  30

Thr Pro Ser Asn Ile Thr Val Leu Asp Val Tyr Lys Thr Pro Ser Leu
        35                  40                  45

Gln Ser Ala Gly His Asp Leu Asn Lys Ile Met Gly Ile Arg Leu Arg
    50                  55                  60

Asn Gly Pro Asp Leu Gln Leu Ser Leu Glu Ser Leu Asp Met Trp Gln
65                  70                  75                  80

Asn Asp Glu Leu Phe Lys Pro Phe Phe His Gln Val Gly Met Ile Asp
                85                  90                  95

Cys Ser Ser Ser Lys Glu Gly Ile Glu Asn Leu Arg Arg Lys Tyr Gln
            100                 105                 110

Thr Leu Leu Asp Ala Gly Ile Gly Leu Glu Lys Thr Asn Val Trp Leu
        115                 120                 125
```

Glu Ser Glu Asp Glu Ile Leu Ala Lys Ala Pro Asn Phe Thr Arg Glu
    130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Ala Gly Thr Phe Gln Gln Pro Leu
                180                 185                 190

Phe Ala Ala Asp Gly Lys Thr Cys Ile Gly Leu Glu Thr Thr Asp Gly
        195                 200                 205

Thr Lys Tyr Phe Ala Asp Lys Val Val Leu Ala Ala Gly Ala Trp Ser
    210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Glu Pro Asn
                260                 265                 270

Glu Tyr Gly Val Ile Lys Val Cys Asp Glu Phe Pro Gly Phe Ser Arg
                275                 280                 285

Phe Lys Leu His Gln Pro Tyr Gly Ala Ala Ser Pro Lys Met Ile Ser
    290                 295                 300

Val Pro Arg Ser His Ala Lys His Pro Thr Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
                340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Leu Leu Pro Asn
    370                 375                 380

Ile Gly Lys His Val Val Glu Leu Leu Glu Gly Ser Leu Ser Gln Glu
385                 390                 395                 400

Met Ala Gly Ala Trp Arg Trp Arg Pro Gly Asp Ala Leu Arg Ser
                405                 410                 415

Arg Arg Gly Ala Pro Ala Lys Asp Leu Ala Glu Met Pro Gly Trp Lys
            420                 425                 430

His Asp Ala His Leu
        435

<210> SEQ ID NO 7
<211> LENGTH: 437
<212> TYPE: PRT
<213> ORGANISM: Coniochaeta spec.

<400> SEQUENCE: 7

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Arg Leu Arg
    50                  55                  60

```
Asn Lys Val Asp Leu Gln Met Ser Leu Glu Ala Arg Gln Met Trp Lys
 65                  70                  75                  80

Glu Asp Glu Leu Phe Gln Pro Phe Phe His Asn Thr Gly Arg Met Asp
                 85                  90                  95

Cys Glu His Thr Pro Gly Ile Glu Asp Leu Lys Lys Gln Tyr Gln
            100                 105                 110

Ala Leu His Asp Ala Gly Ala Gly Leu Glu Lys Thr His Ala Trp Leu
            115                 120                 125

Asp Asn Glu Asp Glu Ile Leu Ser Lys Met Pro Leu Leu Gln Arg Asp
130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
            195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asn
            260                 265                 270

Glu Phe Gly Val Ile Lys Val Cys Asp Glu Phe Pro Gly Phe Ser Arg
            275                 280                 285

Phe Lys Glu His Gln Pro Tyr Gly Ala Pro Ser Pro Lys His Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
            355                 360                 365

Ile Leu Ala Thr Gly Asp Ser Gly His Ser Phe Lys Ile Leu Pro Asn
    370                 375                 380

Val Gly Lys His Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
            435
```

<210> SEQ ID NO 8
<211> LENGTH: 440
<212> TYPE: PRT
<213> ORGANISM: Fusarium oxysporum

<400> SEQUENCE: 8

-continued

```
Ala Ser Thr Leu Thr Lys Gln Ser Gln Ile Leu Ile Val Gly Gly
1               5                   10                  15

Thr Trp Gly Cys Ser Thr Ala Leu His Leu Ala Arg Arg Gly Tyr Thr
            20                  25                  30

Asn Val Thr Val Leu Asp Val Asn Arg Ile Pro Ser Pro Ile Ser Ala
        35                  40                  45

Gly His Asp Val Asn Lys Leu Ala Gly Arg Leu Ser Thr Ala Asp Ser
    50                  55                  60

Lys Gly Asp Asp Glu Asp Ser Ile Trp Lys Ala Leu Ser Tyr Ala Ala
65                  70                  75                  80

Ala Gln Gly Trp Leu His Asp Pro Val Phe Gln Pro Phe Cys His Asn
                85                  90                  95

Thr Gly Ser Val Val Ala Gly Ser Thr Pro Lys Ser Ile Lys Gln Leu
            100                 105                 110

Val Glu Asp Glu Ile Gly Asp Asp Ile Asp Gln Tyr Thr Pro Leu Asn
        115                 120                 125

Thr Ala Glu Asp Phe Arg Lys Thr Met Pro Glu Gly Ile Leu Thr Gly
    130                 135                 140

Asn Phe Pro Gly Trp Lys Gly Phe Tyr Lys Pro Thr Gly Ser Gly Trp
145                 150                 155                 160

Val His Ala Arg Lys Ala Met Lys Ala Ala Phe Glu Glu Ser Glu Arg
                165                 170                 175

Leu Gly Val Lys Phe Ile Thr Gly Ser Pro Glu Gly Lys Val Glu Ser
            180                 185                 190

Leu Ile Phe Glu Asp Gly Asp Val Arg Gly Ala Lys Thr Ala Asp Gly
        195                 200                 205

Lys Glu His Arg Ala Asp Arg Thr Ile Leu Ser Ala Gly Ala Ser Ala
    210                 215                 220

Glu Phe Phe Leu Asp Phe Glu Asn Gln Ile Gln Pro Thr Ala Trp Thr
225                 230                 235                 240

Leu Gly His Ile Gln Met Thr Pro Glu Glu Thr Lys Leu Tyr Lys Asn
                245                 250                 255

Leu Pro Pro Leu Phe Asn Ile Asn Gln Gly Phe Phe Met Glu Pro Asp
            260                 265                 270

Glu Asp Leu His Gln Leu Lys Met Cys Asp Glu His Pro Gly Tyr Cys
        275                 280                 285

Asn Trp Val Glu Lys Pro Gly Ser Lys Tyr Pro Gln Ser Ile Pro Phe
    290                 295                 300

Ala Lys His Gln Val Pro Thr Glu Ala Glu Arg Arg Met Lys Gln Phe
305                 310                 315                 320

Leu Lys Asp Ile Met Pro Gln Leu Ala Asp Arg Pro Leu Val His Ala
                325                 330                 335

Arg Ile Cys Trp Cys Ala Asp Thr Gln Asp Arg Met Phe Leu Ile Thr
            340                 345                 350

Tyr His Pro Arg His Pro Ser Leu Val Ile Ala Ser Gly Asp Cys Gly
        355                 360                 365

Thr Gly Tyr Lys His Ile Thr Ser Ile Gly Lys Phe Ile Ser Asp Cys
    370                 375                 380

Met Glu Gly Thr Leu Glu Glu Arg Phe Ala Lys Phe Trp Arg Trp Arg
385                 390                 395                 400

Pro Glu Lys Phe Thr Glu Phe Trp Gly Lys Asp Pro Leu Asp Arg Phe
                405                 410                 415

Gly Ala Asp Asp Lys Ile Met Asp Leu Pro Lys Ser Asp Val Glu Gly
```

```
                      420             425             430
Trp Thr Asn Ile Lys Asn Asp Ile
        435             440

<210> SEQ ID NO 9
<211> LENGTH: 437
<212> TYPE: PRT
<213> ORGANISM: Aspergillus terreus

<400> SEQUENCE: 9

Met Pro Val Thr Lys Ser Ser Ile Leu Ile Gly Ala Gly Thr
1               5                   10                  15

Trp Gly Cys Ser Thr Ala Leu His Leu Ala Arg Arg Gly Tyr Thr Asn
            20                  25                  30

Val Thr Val Leu Asp Pro Tyr Pro Val Pro Ser Ala Ile Ser Ala Gly
        35                  40                  45

Asn Asp Val Asn Lys Ile Ile Ser Ser Gly Gln Tyr Ser Ser Lys Lys
50                  55                  60

Asp Glu Val Glu Val Asn Glu Ile Ile Ala Glu Gln Ala Phe Asn Gly
65                  70                  75                  80

Trp Lys Asn Asp Pro Ile Phe Lys Pro Tyr Tyr His Asp Thr Gly Val
                85                  90                  95

Val Met Ser Ala Thr Thr Gln Glu Gly Leu Glu Arg Leu Gly Val Arg
            100                 105                 110

Val Arg Pro Glu Asp Glu Pro Asp Val Ala Glu Leu Thr Arg Pro Glu
        115                 120                 125

Gln Phe Arg Gln Leu Ala Pro Gly Val Leu Lys Gly Asn Phe Pro Gly
    130                 135                 140

Trp Arg Gly Tyr His Ile Arg Ser Asn Ala Gly Trp Ala His Ala Arg
145                 150                 155                 160

Asn Ala Leu Val Ala Ala Ala Arg Glu Ala Gln Arg Leu Gly Val Arg
                165                 170                 175

Phe Val Ala Gly Ser Pro Gln Gly Arg Val Ile Thr Leu Ile Phe Glu
            180                 185                 190

Asn Asn Asp Val Lys Gly Ala Val Thr Ala Asp Gly Lys Ile Trp Arg
        195                 200                 205

Ala Glu Gln Thr Ile Leu Cys Ala Gly Ala Ala Gly Gln Phe Leu
    210                 215                 220

Asp Phe Lys Asp Gln Leu Arg Pro Thr Ala Trp Thr Leu Val His Ile
225                 230                 235                 240

Gln Leu Lys Pro Glu Glu Arg Ala Gln Tyr Lys Asn Met Pro Val Val
                245                 250                 255

Phe Asn Ile Glu Lys Gly Phe Phe Glu Pro Asp Glu Glu Arg Gly
            260                 265                 270

Glu Ile Lys Ile Cys Asp Glu His Pro Gly Tyr Thr Asn Met Thr Thr
        275                 280                 285

Gly Ala Asp Gly Arg Val Arg Ser Ile Pro Phe Glu Lys Thr Gln Val
    290                 295                 300

Pro Arg Glu Ala Glu Met Arg Val Arg Lys Leu Leu Ser Glu Thr Met
305                 310                 315                 320

Pro Gln Leu Ala Asp Arg Pro Phe Ser Phe Ala Arg Ile Cys Trp Cys
                325                 330                 335

Ala Asp Thr Pro Asn Arg Glu Phe Ile Ile Asp Arg His Pro Glu Tyr
            340                 345                 350

Pro Ser Leu Val Leu Gly Cys Gly Ala Ser Gly Arg Gly Phe Lys Tyr
```

```
                355                 360                 365
Leu Pro Ser Ile Gly Ser Ile Ile Ala Asp Ala Met Glu Asp Lys Thr
370                 375                 380

Pro Ala Lys Ile His Lys Leu Ile Arg Trp Ser Pro Glu Ile Ala Ile
385                 390                 395                 400

Asn Arg Asn Trp Gly Asp Arg Leu Gly Arg Phe Gly Pro Asn Arg
                405                 410                 415

Val Met Asp Phe Asn Glu Val Lys Glu Trp Thr Asn Val Thr Gln Arg
                420                 425                 430

Asp Ile Ser Lys Leu
            435

<210> SEQ ID NO 10
<211> LENGTH: 445
<212> TYPE: PRT
<213> ORGANISM: Aspergillus oryzae

<400> SEQUENCE: 10

Met Thr Ser Ser Lys Leu Thr Pro Thr Ser Ile Leu Ile Val Gly
1               5                   10                  15

Ala Gly Thr Trp Gly Cys Ser Thr Ala Leu His Leu Ala Arg Arg Gly
                20                  25                  30

Tyr Lys Asn Val Thr Val Leu Asp Pro His Pro Val Pro Ser Pro Ile
                35                  40                  45

Ala Ala Gly Asn Asp Ile Asn Lys Ile Met Glu His Arg Glu Val Lys
                50                  55                  60

Ala Ser Glu Thr Asp Pro Trp Ser Ile Ala Phe Ser Thr Cys Thr Arg
65                  70                  75                  80

Ala Ala Leu Lys Gly Trp Lys Asn Asp Pro Val Phe Gln Pro Tyr Phe
                85                  90                  95

His Glu Thr Gly Ala Ile Val Ser Gly His Thr Ala Ser Leu Ile Lys
                100                 105                 110

His Ile Gln Glu His Glu Ile Asp Ser Ser Asp Ala Glu Phe Ile Lys
                115                 120                 125

Leu Asn Thr Ala Glu Asp Phe Arg Lys Thr Met Pro Pro Gly Ile Leu
130                 135                 140

Thr Gly Asn Phe Pro Gly Trp Lys Gly Trp Leu Asn Lys Thr Gly Ala
145                 150                 155                 160

Gly Trp Ile His Ala Lys Lys Ala Met Phe Ser Ala Tyr Thr Glu Ala
                165                 170                 175

Lys Arg Leu Gly Val Thr Phe Ile Thr Gly Ser Pro Glu Gly Asp Val
                180                 185                 190

Val Ser Leu Ile Tyr Glu Asn Gly Asp Val Val Gly Ala Arg Thr Ala
                195                 200                 205

Asp Gly Thr Val His Arg Ala Asp His Thr Ile Leu Ser Ala Gly Ala
                210                 215                 220

Gly Ser Asp Arg Leu Leu Asp Phe Lys Lys Gln Leu Arg Pro Thr Ala
225                 230                 235                 240

Trp Thr Leu Cys His Ile Arg Met Thr Pro Asp Glu Ala Lys Lys Tyr
                245                 250                 255

Arg Asn Leu Pro Val Leu Phe Asn Val Ala Lys Gly Phe Phe Met Glu
                260                 265                 270

Pro Asp Glu Asp Asn His Glu Leu Lys Ile Cys Asp Glu His Pro Gly
                275                 280                 285

Tyr Cys Asn Phe Val Pro Asp Pro Lys His Gly Gly Glu Val Arg Ser
```

```
                    290                 295                 300
Ile Pro Phe Ala Lys His Gln Ile Pro Leu Glu Ala Glu Ala Arg Ala
305                 310                 315                 320

Arg Asp Phe Leu Arg Asp Thr Met Pro His Leu Ala Asp Arg Pro Leu
                    325                 330                 335

Ser Phe Ala Arg Ile Cys Trp Asp Ala Asp Thr Val Asp Arg Ala Phe
                    340                 345                 350

Leu Ile Asp Arg His Pro Glu Tyr Arg Ser Leu Leu Ala Val Gly
                    355                 360                 365

Gly Ser Gly Asn Gly Ala Met Gln Met Pro Thr Ile Gly Gly Phe Ile
                    370                 375                 380

Ala Asp Ala Leu Glu Gly Asn Leu Gln Lys Glu Leu Lys His Ala Leu
385                 390                 395                 400

Arg Trp Arg Pro Glu Ile Ala Ala Gln Arg Asp Trp Lys Asp Thr Gln
                    405                 410                 415

Asn Arg Phe Gly Gly Pro Asn Lys Val Met Asp Phe Gln Lys Val Gly
                    420                 425                 430

Glu Asn Glu Trp Thr Lys Ile Gly Asp Lys Ser Arg Leu
                    435                 440                 445

<210> SEQ ID NO 11
<211> LENGTH: 445
<212> TYPE: PRT
<213> ORGANISM: Aspergillus fumigatus

<400> SEQUENCE: 11

Met Ala Pro Ser Ile Leu Ser Thr Glu Ser Ile Ile Val Ile Gly
1               5                   10                  15

Ala Gly Thr Trp Gly Cys Ser Thr Ala Leu His Leu Ala Arg Arg Gly
                    20                  25                  30

Tyr Lys Asp Val Thr Val Leu Asp Pro His Pro Val Pro Ser Pro Ile
                    35                  40                  45

Ala Ala Gly Asn Asp Ile Asn Lys Ile Met Glu His Ser Glu Leu Lys
                    50                  55                  60

Asp Gly Ser Ser Asp Pro Arg Ser Ala Ala Phe Ser Thr Phe Thr Arg
65                  70                  75                  80

Ala Ala Leu Lys Ala Trp Lys Thr Asp Pro Val Phe Gln Pro Tyr Phe
                    85                  90                  95

His Glu Thr Gly Phe Ile Ile Ser Gly His Thr Pro Ala Leu Ile Asp
                    100                 105                 110

His Ile Arg Lys Asp Glu Val Glu Pro Ser Glu Thr Asn Phe Val Lys
                    115                 120                 125

Leu Glu Thr Ala Glu Asp Phe Arg Arg Thr Met Pro Pro Gly Val Leu
                    130                 135                 140

Thr Gly Asp Phe Pro Gly Trp Lys Gly Trp Leu His Lys Ser Gly Ala
145                 150                 155                 160

Gly Trp Ile His Ala Lys Lys Ala Met Ile Ser Ala Phe Asn Glu Ala
                    165                 170                 175

Lys Arg Leu Gly Val Arg Phe Val Thr Gly Ser Pro Glu Gly Asn Val
                    180                 185                 190

Val Ser Leu Val Tyr Glu Asp Gly Asp Val Val Gly Ala Arg Thr Ala
                    195                 200                 205

Asp Gly Arg Val His Lys Ala His Arg Thr Ile Leu Ser Ala Gly Ala
                    210                 215                 220

Gly Ser Asp Ser Leu Leu Asp Phe Lys Lys Gln Leu Arg Pro Thr Ala
```

```
                    225                 230                 235                 240

Trp Thr Leu Cys His Ile Gln Met Gly Pro Glu Glu Val Lys Gln Tyr
                    245                 250                 255

Arg Asn Leu Pro Val Leu Phe Asn Ile Ala Lys Gly Phe Phe Met Glu
                260                 265                 270

Pro Asp Glu Asp Lys His Glu Leu Lys Ile Cys Asp Glu His Pro Gly
            275                 280                 285

Tyr Cys Asn Phe Leu Pro Asp Pro Asn Arg Pro Gly Gln Glu Lys Ser
        290                 295                 300

Val Pro Phe Ala Lys His Gln Ile Pro Leu Glu Ala Glu Ala Arg Ala
305                 310                 315                 320

Arg Asp Phe Leu His Asp Thr Met Pro His Leu Ala Asp Arg Pro Leu
                325                 330                 335

Ser Phe Ala Arg Ile Cys Trp Asp Ala Asp Thr Pro Asp Arg Ala Phe
            340                 345                 350

Leu Ile Asp Arg His Pro Glu His Pro Ser Leu Leu Val Ala Val Gly
        355                 360                 365

Gly Ser Gly Asn Gly Ala Met Gln Met Pro Thr Ile Gly Gly Phe Ile
    370                 375                 380

Ala Asp Ala Leu Glu Ser Lys Leu Gln Lys Glu Val Lys Asp Ile Val
385                 390                 395                 400

Arg Trp Arg Pro Glu Thr Ala Val Asp Arg Asp Trp Arg Ala Thr Gln
                405                 410                 415

Asn Arg Phe Gly Gly Pro Asp Arg Ile Met Asp Phe Gln Gln Val Gly
            420                 425                 430

Glu Asp Gln Trp Thr Lys Ile Gly Glu Ser Arg Gly Pro
        435                 440                 445

<210> SEQ ID NO 12
<211> LENGTH: 436
<212> TYPE: PRT
<213> ORGANISM: Aspergillus oryzae

<400> SEQUENCE: 12

Met Thr Val Ala Lys Ser Ser Ile Leu Ile Ile Gly Ala Gly Thr
1               5                   10                  15

Trp Gly Ala Ser Thr Ala Leu His Leu Gly Arg Arg Gly Tyr Thr Asn
                20                  25                  30

Val Thr Val Leu Asp Pro Tyr Thr Val Pro Ser Ala Ile Ser Ala Gly
            35                  40                  45

Asn Asp Val Asn Lys Ile Ile Ser Ser Gly Gln Tyr Ser Asn Lys Lys
        50                  55                  60

Asp Glu Ile Glu Val Asn Glu Ile Leu Ala Glu Ala Phe Lys Gly
65                  70                  75                  80

Trp Thr Thr Asp Pro Leu Phe Lys Pro Tyr Tyr His Asp Thr Gly Val
                85                  90                  95

Val Met Ser Ala Cys Ser Ser Ala Gly Leu Asp Arg Leu Gly Ile Arg
            100                 105                 110

Val Arg Pro Glu Glu Glu Pro Asp Val Ser Glu Val Thr Lys Pro Glu
        115                 120                 125

His Phe Arg Gln Leu Ala Pro Ala Val Leu Lys Gly Asn Phe Pro Gly
    130                 135                 140

Trp Arg Gly Tyr His Ile Arg Ser Asn Ala Gly Trp Ala His Ala Arg
145                 150                 155                 160

Asn Ala Leu Val Ala Ala Ile Arg Glu Ala Glu Lys Leu Gly Val Lys
```

```
            165                 170                 175
Phe Val Thr Gly Thr Gln Gly Arg Val Ile Thr Leu Ile Phe Glu Asn
        180                 185                 190

Asn Asp Val Lys Gly Ala Val Thr Ala Asp Gly Lys Ile Trp Arg Ala
        195                 200                 205

Glu Gln Thr Val Leu Cys Ala Gly Ala Asn Ala Ala Gln Phe Leu Asp
        210                 215                 220

Phe Lys Asp Gln Leu Arg Pro Thr Ala Trp Thr Leu Ala His Ile Arg
225                 230                 235                 240

Leu Lys Pro Glu Glu Arg Ala Leu Tyr Lys Asn Leu Pro Val Ile Phe
                245                 250                 255

Asn Ile Glu Lys Gly Phe Phe Phe Glu Pro Asp Glu Glu Arg Gly Glu
            260                 265                 270

Ile Lys Ile Cys Asp Glu His Pro Gly Tyr Thr Asn Met Val Lys Ser
        275                 280                 285

Ala Asp Gly His Leu Thr Ser Leu Pro Phe Glu Lys Thr Gln Ile Pro
        290                 295                 300

Lys Glu Ser Glu Ala Arg Val Arg Ala Leu Leu Ser Glu Thr Met Pro
305                 310                 315                 320

Gln Leu Ala Asp Arg Pro Phe Ser Phe Ala Arg Val Cys Trp Cys Ala
                325                 330                 335

Asp Thr Ala Asn Arg Glu Phe Ile Ile Asp Arg His Pro Glu His Pro
            340                 345                 350

Ser Leu Val Leu Gly Cys Gly Ala Ser Gly Arg Gly Phe Lys Tyr Leu
        355                 360                 365

Pro Ser Ile Gly Asn Leu Ile Val Asp Ala Ile Glu Asp Lys Val Pro
    370                 375                 380

Glu Lys Val His Lys Leu Thr Arg Trp Ser Pro Asp Ile Ala Val Asp
385                 390                 395                 400

Arg Lys Trp Arg Asp Thr Leu Gly Arg Phe Gly Gly Pro Asn Arg Val
                405                 410                 415

Met Asp Phe His Asp Val Lys Glu Trp Thr Asn Val Gln Asn Lys Asp
            420                 425                 430

Thr Ala Lys Leu
        435

<210> SEQ ID NO 13
<211> LENGTH: 12
<212> TYPE: PRT
<213> ORGANISM: Phaeosphaeria nodorum

<400> SEQUENCE: 13

Val Ser Leu Arg Asn Pro Val Asp Leu Gln Leu Ala
1               5                   10

<210> SEQ ID NO 14
<211> LENGTH: 12
<212> TYPE: PRT
<213> ORGANISM: Coniochaeta spec.

<400> SEQUENCE: 14

Ile Arg Leu Arg Asn Lys Val Asp Leu Gln Met Ser
1               5                   10

<210> SEQ ID NO 15
<211> LENGTH: 16
<212> TYPE: PRT
<213> ORGANISM: Phaeosphaeria nodorum
```

```
<400> SEQUENCE: 15

Ser Gly Tyr Gln Ala Leu Val Asp Ala Gly Leu Asp Ala Thr Asn Glu
1               5                   10                  15

<210> SEQ ID NO 16
<211> LENGTH: 18
<212> TYPE: PRT
<213> ORGANISM: Coniochaeta spec.

<400> SEQUENCE: 16

Lys Gln Tyr Gln Ala Leu His Asp Ala Gly Ala Gly Leu Glu Lys Thr
1               5                   10                  15

His Ala
```